United States Patent [19]
Bretscher et al.

[11] Patent Number: 5,714,122
[45] Date of Patent: Feb. 3, 1998

[54] EMULSION FOR ROBUST SENSING

[75] Inventors: Kathryn R. Bretscher, St. Paul, Minn.;
James A. Baker, Hudson, Wis.;
Kenneth B. Wood, St. Paul, Minn.;
Mai T. Nguyen, Maplewood, Minn.;
Monica A. Hamer, Woodbury, Minn.;
Christopher J. Rueb, St. Paul, Minn.

[73] Assignee: Minnesota Mining and Manufacturing Company, St. Paul, Minn.

[21] Appl. No.: 562,036

[22] Filed: Nov. 22, 1995

[51] Int. Cl.⁶ .................................................. G01N 21/64
[52] U.S. Cl. .................................. 422/82.07; 422/82.08; 436/166
[58] Field of Search ......................... 422/82.05, 82.06, 422/82.07, 82.08; 436/172, 164, 166, 167

[56] References Cited

U.S. PATENT DOCUMENTS

| | | | |
|---|---|---|---|
| Re. 31,879 | 5/1985 | Lübbers et al. | 436/133 |
| 4,510,094 | 4/1985 | Drahnak | 260/429 CY |
| 4,530,879 | 7/1985 | Drahnak | 428/352 |
| 4,557,900 | 12/1985 | Heitzmann | 422/55 |
| 4,640,820 | 2/1987 | Cooper | 422/68 |
| 4,786,474 | 11/1988 | Cooper | 422/68 |
| 4,824,789 | 4/1989 | Yafuso et al. | 436/68 |
| 4,840,485 | 6/1989 | Gratton | 356/317 |
| 4,867,919 | 9/1989 | Yafuso et al. | 264/1.5 |
| 4,916,169 | 4/1990 | Boardman et al. | 522/27 |
| 4,925,268 | 5/1990 | Iyer et al. | 422/82.07 |
| 5,145,886 | 9/1992 | Oxman et al. | 522/66 |
| 5,175,016 | 12/1992 | Yafuso et al. | 427/2 |
| 5,219,527 | 6/1993 | Hui et al. | 422/82.06 |
| 5,284,775 | 2/1994 | Yafuso et al. | 436/68 |
| 5,403,746 | 4/1995 | Bentsen et al. | 422/82.07 |
| 5,409,666 | 4/1995 | Nagel et al. | 422/82.07 |
| 5,462,879 | 10/1995 | Bentsen | 436/136 |
| 5,508,509 | 4/1996 | Yafuso et al. | 422/82.05 |

FOREIGN PATENT DOCUMENTS

| | | |
|---|---|---|
| 0 105 870 | 2/1987 | European Pat. Off. . |
| 0 319 863 | 6/1989 | European Pat. Off. . |
| 0 597 566 A1 | 5/1994 | European Pat. Off. . |

OTHER PUBLICATIONS

Noriyoshi Kaya and Masumi Koishi, "The Wetting Properties of Powders and Devices for Measuring Them"; *Kona*, No. 6 (1988) pp. 86–97.

*Handbook of Fluorescent Probes and Research Chemicals*, Richard P. Haugland, 5th Ed., 1992, pp. 129–141.

"Calculation of HLB Values of Non–Ionic Surfactants", William C. Griffin, *Journal of the Society of Cosmetic Chemists*, 5 (1954) pp. 249–256.

"Classification of Surface–active Agents by HLB", William C. Griffin, *Journal of the Society of Cosmetic Chemists*, 1 (1949) pp. 311–326.

"Characterization of silica surfaces hydrophobized by octadecyltrichlorosilane", D.H. Flinn, D.A. Guzonas, R.–H. Yoon, *Colloids and Surfaces A: Physicochemical and Engineering Aspects*, 87(1994) pp. 163–176.

"Hydrophile–Lipophile Balance and Cloud Points of Nonionic Surfactants", Hans Schott, *Journal of Pharmaceutical Sciences*, vol. 58, No. 12, Dec. 1969, pp. 1443–1449.

(List continued on next page.)

*Primary Examiner*—Jeffrey Snay
*Attorney, Agent, or Firm*—Gary L. Griswold; Walter N. Kirn; F. Andrew Ubel

[57] ABSTRACT

The present invention provides an optical fluorescence based sensor for measuring the concentration of a gas (e.g., $CO_2$ or ammonia) in a medium such as blood which has superior dry web sensor performance, enhanced sensor consistency for transparent sensor calibration, improved autoclave stability and rapid rehydration of the sensor. In a preferred embodiment, the sensors of the present invention comprise microcompartments of an aqueous phase having a pH sensitive indicator component and a nonionic amphipathic surfactant within a hydrophobic barrier phase comprising a plurality of dispersed hydrophobic particles.

47 Claims, 6 Drawing Sheets

OTHER PUBLICATIONS

"The Determination of Hydrophile–Lipophile Balance by Gas–Liquid Chromatography", Paul Becher and R.L. Birkmeier, *The Journal of the American Oil Chemists' Society*, vol. 41 (1964) pp. 169–172.

*Encyclopedia of Emulsion Technology*, Tharwat F. Tadros and Brian Vincent, vol. 1, Edited by Paul Becher (1983) pp. 129–285.

UCON™ product literature, p. 3.

Hypermer product literature, p. 10.

"Emulsification by Surfactants", *Surfactants and Interfacial Phenomena*, Milton J. Rosen (1978) pp. 224–250.

Remington's Pharmaceutical Sciences, Mack Publishing Company, 1965, Chapter 18, pp. 264–265.

"Association Colloids and Self–Assembly Systems", *Basic Principles of Colloid Science*, D. H. Everett, Chapter 11, pp. 154–155.

Hawley's Condensed Chemical Disctionary, Twelfth Edition, Revised by Richard J. Lewis,s Sr., Van Nostrand Reinhold Company, New York, p. 608.

"Macroemulsions", Paul Becher, Martin Schick, *Nonioinc Surfactants Physical Chemistry*, 1987, Chapter 8, pp. 435–491.

"HLB of Nonionic Surfactants: PIT and EIP Methods", Leszek Marszall, *Nonionic Surfactants Physical Chemistry*, 1987, Chapter 9, pp. 494–547.

"Characteristic Features of Surfactants", *Surfactants and Interfacial Phenomena*, Milton J. Rosen, 1978, Chapter 1, pp. 1–3.

*Surfactants and Interfacial Phenomena*, Milton J. Rosen, 1978, pp. 236–237.

*Principles of Colloid and Surface Chemistry*, Second Edition, Paul C. Hiemenz, 1986, p. 451.

*Dispersing Powders In Liquids*, Ralph D. Nelson, Jr., 1988, p. 145.

Silwet Surfactants, Osi Specialties, Inc., 1994, pp. 1–20.

Cab–O–Sil® TS–530, Cabot Corporation, 1991 Technical Data.

Pluronic & Tetronic Surfactants, BASF, BASF Corporation, 1989, pp. 2–29.

"Clues to Surfactant Selection Offered by HLB System", W.C. Griffin, *Official Digest Fed. Paint and Varnish Production Clubs*, Jun. 1956, pp. 446–455.

"Fundamental principles of emulsion rheology and their applications", Th.F. Tadros, *Colloids ands Surfaces Physicochemical and Enginering Aspects*, 91 (1994), pp. 39–55.

"Emulsions and Foams", Duncan J. Shaw, *Introduction to Colloid and Surface Chemistry*, Butterworths 1980, pp. 232–245.

EMULSION FOR ROBUST SENSING

FIELD

The present invention relates generally to sensors for measuring the concentration of an analyte of interest. In a preferred embodiment, the present invention relates to sensors for monitoring blood gas concentrations (e.g., carbon dioxide). The present invention also relates to methods of making stable and reproducible water in oil emulsions comprised of a dispersed aqueous phase and a hydrophobic continuous phase.

BACKGROUND

It is sometimes necessary or desirable for a physician to determine the concentration of certain gases, e.g., oxygen and carbon dioxide, in blood. This can be accomplished utilizing an optical sensor which contains an optical indicator responsive to the component or analyte of interest. The optical sensor is exposed to the blood, and excitation light is provided to the sensor so that the optical indicator can provide an optical signal indicative of a characteristic of the analyte of interest. For example, the optical indicator may fluoresce and provide a fluorescent optical signal or it may function on the principles of light absorbance.

The use of optical fibers has been suggested as part of such sensor systems. The optical indicator is placed at the end of an optical fiber which is placed in contact with the medium to be analyzed. This approach has many advantages, particularly when it is desired to determine a concentration of analyte in a medium inside a patient's body. The optical fiber/indicator combination can be made sufficiently small in size to easily enter and remain in the cardiovascular system of the patient.

Optical fluorescence $CO_2$ sensors commonly utilize an indirect method of sensing based on the hydration of $CO_2$ to form carbonic acid within an optionally buffered aqueous compartment containing a pH sensitive dye. The aqueous compartment is encapsulated in a barrier material which is impermeable to hydrogen ions but permeable to $CO_2$. An optically interrogated pH change in the internal aqueous compartment can then be related to the partial pressure of $CO_2$ in the monitored sample. Ionic isolation of the internal aqueous phase may be achieved by directly dispersing aqueous droplets throughout the isolating matrix. Alternatively, the aqueous phase may be sorbed into porous particles which are then dispersed throughout the isolating matrix. The isolation matrix or "barrier" is typically a crosslinked silicone polymer.

Unfortunately, prior attempts to provide stable and reproducible emulsions of an aqueous phase dispersed in a polymeric precursor have yielded poor results. In some cases, the emulsions exhibited unexplained lot-to-lot variability that frustrate attempts to perform quantitative experiments correlating sensor performance to the particular sensor formulation. Variability within lots has also been observed. This variability frustrates attempts to uniformly produce sensors, e.g., by coating a sheet of sensor precursor and converting the sheet into individual Sensor elements. In other cases, the emulsoids formed from the emulsions are adversely affected by heat (e.g., during autoclaving) and the sensor's performance is thereby compromised. Also unfortunately, prior attempts to make sensors that respond to $CO_2$ in the "dry" state, i.e., not in contact with liquid water, have yielded poor results. Traditional two-phase sensors dehydrate when stored in ambient conditions and lose intensity. Even when intensity is maintained in the dry state, the sensor may not respond to $CO_2$.

It would be desirable to provide a stable and reproducible sensor which has a fast response time and which is easily manufactured. It would also be desirable to provide a $CO_2$ sensor that provides a stable and effective signal that does not require that it be held in a condition of equilibrium with liquid water or saturated water vapor.

SUMMARY

We have discovered a stable and reproducible sensor. This sensor employs the preparation of stable water in oil emulsions comprised of a dispersed aqueous phase and a hydrophobic continuous phase. More specifically, this invention provides a novel method of preparing aggregation and coalescence resistant emulsions for use as blood gas sensor compositions, and further discloses novel emulsion compositions suitable for use in consistently and uniformly manufacturing precision coated blood gas sensors.

In one embodiment, the invention provides a gas sensing composition, comprising a dispersed first phase comprising droplets which are substantially smaller in at least one dimension than the thickness of the sensing composition and a hydrophobic second phase which is permeable to the analyte and impermeable to ionized hydrogen. The first phase contains at least one substantially water soluble emulsification enhancement agent and at least one water soluble indicator component effective to provide a signal in response to the concentration of a gas in a medium to which the sensing composition is exposed. The second phase contains at least one substantially water insoluble emulsification enhancement agent. Preferably the water soluble emulsification enhancement agent comprises a nonionic, amphipathic copolymer containing both hydrophilic and hydrophobic moieties, and the water insoluble emulsification enhancement agent comprises a plurality of dispersed hydrophobic particles.

The improved sensor compositions exhibit superior dry web sensor performance, enhanced sensor consistency for transparent sensor calibration, improved autoclave stability and rapid rehydration of the sensor.

The improved sensors may be used to sense the concentration of an analyte of interest in a medium. More particularly, the improved sensors may be used to sense carbon dioxide in blood. The invention also relates to sensor apparatus or systems and methods for sensing the concentration of other analytes of interest in industrial settings and environments (e.g., ammonia, $CO_2$, $SO_2$, or $NO_2$).

Precision coated blood gas sensors are provided which exhibit improved coating uniformity and consistent sensor performance from lot to lot, thereby increasing the yield of usable sensors and permitting transparent calibration of the sensors independent of coating time or lot. By transparent calibration we mean the designation of a sensor web lot by the manufacturer according to its calibration parameters (slope and/or intercept) achieved by a web sampling plan. Transparent calibration allows the user to use a constant set of calibration parameters and significantly reduces the calibration time required by the user. It is dependent on consistent performance across and down sensor webs.

In another embodiment, the present invention provides a "dry" gas sensing composition, comprising a dispersed first phase containing a humectant (preferably glycerol) and at least one soluble indicator component; and a hydrophobic second phase which is permeable to the analyte and impermeable to ionized hydrogen. The first phase optionally contains a water soluble emulsification enhancement agent as described above. The second phase optionally, and preferably, contains at least one substantially water insoluble emulsification enhancement agent. The sensing composition of this embodiment provides an effective signal in response to the gas without the necessity that it be held in a condition of equilibrium with liquid water or water vapor prior to use.

In yet another embodiment, the present invention provides a precision coated blood gas sensor which exhibits improved autoclave stability, and preferably also exhibits improved dry web shelf stability. Most preferred blood gas sensors also exhibit rapid rehydration rates.

RELATED APPLICATIONS

Of related interest are copending U.S. patent applications Ser. No. 08/375,304, now U.S. Pat. No. 5,607,645, "Sensor with Improved Drift Stability"; Ser. No. 08/159,799, now U.S. Pat. No. 5,508,509, "Sensing Elements and Methods for Making Same"; Ser. No. 08/136,967, now U.S. Pat. No. 5,462,879,"Emission Quenching Sensors"; and Ser. No. 08/137,289, now U.S. Pat. No. 5,409,666, "Sensors and Methods for Sensing," the disclosures of which are herein incorporated by reference.

BRIEF DESCRIPTION OF THE DRAWINGS

This invention will be better understood when taken in conjunction with the drawings wherein.

Figure 1:
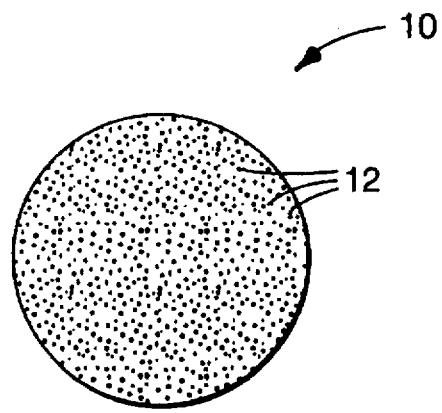
FIG. 1 is an elevational view in section of a droplet of material utilized in the preparation of a gas sensor of the invention.

This invention utilizes certain principles and/or concepts as are set forth in the claims appended to this specification. Those skilled in the gas sensing arts to which this invention pertains will realize that these principles and/or concepts are capable of being illustrated in a variety of embodiments which may differ from the exact embodiments utilized for illustrative purposes in this specification. For these reasons, the invention described in this specification is not to be construed as being limited to only the illustrative embodiments but is only to be construed in view of the appended claims.

DEFINITIONS

As used herein, the terms "aqueous first phase" or "aqueous phase" refer to the hydrophilic phase or phases of a multiphase sensor which comprises an indicator component ("dye") and which more preferably, but not necessarily, further comprises water.

As used herein, the terms "hydrophobic second phase" or "hydrophobic phase" refer to that phase of a multiphase sensor which separates an aqueous phase (comprising an indicator component) from the medium containing the analyte of interest. As used herein, the terms "polymeric phase" or "silicone phase" refer to a hydrophobic second phase which comprises a polymer material or silicone material, respectively.

As used herein, the term "medium" refers to the solid, liquid, or gaseous environment to which the sensor is exposed. For example, sensors are often placed into a medium of blood so that the blood gasses (e.g., $CO_2$ level) may be measured. Sensors may also be placed in a gas (or $CO_2$) equilibrated liquid medium (e.g., to calibrate a sensor).

As used herein, the term "emulsion" refers to a uniform multi-phase system of two or more liquids and includes multi-phase suspensions and dispersions of droplets of one liquid, comprising the dispersed or internal phase, in a second substantially insoluble and immiscible liquid, comprising the continuous or external phase. The use of the term emulsion is not limited to thermodynamically stable mixtures or mixtures containing emulsifiers. As used herein, the term "stable emulsion" refers to emulsions which remain substantially uniform (macroscopically) for a long enough period of time to allow the emulsion to be formed into the desired configuration, e.g., a period of at least several hours. As used herein, the term "thermodynamically stable emulsion" refers to emulsions which remain substantially uniform (macroscopically) even when heated and then cooled.

As used herein, the term "emulsoid" refers to a multi-phase system comprising micro-compartments of a dispersed phase in a second solid phase (e.g., a cross-linked polymer phase).

As used herein, the terms "emulsification enhancement agent" (EEA) or "emulsifier" refer to a substance which acts alone or together with another emulsification enhancement agent or emulsifier to facilitate the formation and promote the stability of an emulsion.

As used herein, the terms "surface active agent" or "surfactant" refer to chemical substances which are strongly adsorbed at an interface, thereby causing a substantial lowering of the surface (or interfacial) tension.

As used herein, the term "amphipathic compound" refers to a molecular structure characteristic of surface active agents which form micelles. Amphipathic molecules consist of a chemical structural group (the lyophobic group) having very little affinity for the solvent (hence low solubility in that solvent), combined with a chemical structural group (the lyophilic group) having very high affinity for the solvent (hence high solubility in that solvent). When the solvent is water or predominantly aqueous, the lyophobic group is described as hydrophobic and the lyophilic group is described as hydrophilic.

As used herein, the term "cloud point" refers to the maximum temperature at which micelles are stable with respect to aggregation. At temperatures above the cloud point, micelles will either coalesce into an insoluble bulk surfactant phase, or aggregate and settle into a concentrated sediment of large miceliar aggregates. The cloud point is marked by a change in physical appearance from a visually transparent solution to a visually turbid, multiphase dispersion.

As used herein, the term "hydrophile-lipophile balance" (HLB) refers to an empirical scale ranging from 0 to 40 used for representing the amphipathic nature of a surface active agent. Low values correspond to more hydrophobic surfactants, while high values correspond to more hydrophilic surfactants. For nonionic surfactants which do not contain a polyoxypropylene, polyoxybutylene or polydimethylsiloxane group, the HLB is determined using the methods of Griffin [Griffin, W. C., J. Soc. Cosmetic Chemists, 1, 311 (1949), Griffin, W. C., J. Soc. Cosmetic Chemists, 5, 249 (1954).]. For nonionic surfactants containing the polyoxypropylene or polyoxybutylene groups, the HLB is determined by measuring gas-liquid chromatography (GLC) relative retention ratios using the method of Becher and Birkmeier (Becher, P. and Birkmeier, R. L., *J. Am. Oil Chemists Soc.*, 41, 169 (1964).]. For nonionic surfactants containing the polydimethylsiloxane group in conjunction with polyoxyethylene, polyoxypropylene or polyoxybutylene, the HLB is determined from cloud point measurements using the method of Griffin [Griffin, W. C., *Off. Dig. Fed. Paint and Varnish Production Clubs*, 28, 446 (1956); and Schott, H., *J. Pharm. Science*, 58, 1443 (1969) (citing Griffm)]. The aforementioned references are herein incorporated by reference.

As used herein, the term "hydrophilic particle" refers to a finely-divided, substantially water insoluble solid, with a mean volume average diameter less than 5 microns, the surface of which may be treated with an organic compound and which exhibits a high affinity for water, as reflected by a solid/liquid contact angle (measured through the aqueous phase) of less than 90 degrees.

As used herein, the term "hydrophobic particle" refers to a finely-divided, substantially water insoluble solid, with a mean volume average diameter less than 5 microns, the surface of which may be treated with an organic compound and which exhibits a low affinity for water, as reflected by a solid/liquid contact angle (measured through the aqueous phase) of greater than 90 degrees.

As used herein, the term "micelle" refers to an organized cluster of amphipathic surfactant molecules dissolved in a solvent, in which the lyophobic groups of the individual molecules are oriented towards the interior of the cluster (i.e., away from the solvent), and the lyophilic groups of the individual molecules are oriented towards the exterior of the cluster (i.e., towards the solvent). The concentration of surfactant above which micelle formation becomes appreciable is defined as the critical micelle concentration, and is marked by a plateau of nearly concentration independent osmotic pressure and surface tension of the solution.

As used herein, the term "partitioning species" refers to those species, other than the analyte of interest, which can migrate from the aqueous phase to the hydrophobic phase (or vice versa) in response to a change in pH in the aqueous phase and which substantially affect the concentration dependent signal (i.e., the signal provided by the indicator component which is proportional to the concentration of the analyte of interest in the medium being measured). A material is "substantially free" of partitioning species when the species are no longer capable of substantially affecting the concentration dependent signal.

As used herein, the term "response time" refers to the time necessary for the concentration dependent signal of a given sensor to reflect the concentration of the analyte of interest when the sensor is exposed to the medium containing the analyte. The response time includes any time necessary for the sensor to stabilize to the medium, but does not include the time over which migration of partitioning species occurs to introduce drift.

DETAILED DESCRIPTION

The sensors of the present invention comprise an emulsoid of a dispersed aqueous first phase in a hydrophobic second phase.

The sensors are formed from a stable emulsion of the dispersed aqueous first phase and a hydrophobic second phase precursor. Preferably, the aqueous first phase includes an indicator component in a buffer solution, and a water soluble emulsification enhancement agent preferably comprising a nonionic amphipathic surfactant. Preferably, the hydrophobic second phase contains a polymeric precursor having a water insoluble emulsification enhancement agent comprising a plurality of dispersed hydrophobic particles. The hydrophobic second phase is permeable to the analyte of interest and impermeable to ionized hydrogen.

The emulsion may contain humectants that may enhance the sensor properties, e.g., imparting dry web stability, rapid rehydration, and response to atmospheric $CO_2$. The emulsion can be readily formed into a variety of shapes, as described herein, and is polymerized or hardened to form an emulsoid.

In a presently preferred embodiment, a solution or dispersion of a suitable indicator dye is formed in an aqueous buffer. The aqueous mixture preferably further comprises a water soluble emulsification enhancement agent comprising a nonionic amphipathic surfactant. The aqueous mixture is then emulsified with (or uniformly dispersed or suspended with) a liquid precursor of a polymeric material and a water insoluble emulsification enhancement agent preferably comprising a plurality of dispersed hydrophobic particles. During the emulsification or suspension step, the aqueous phase is broken up into very small droplet sizes. The polymeric material is chosen such that the aqueous phase is not readily soluble in either the precursor materials for the polymeric material or the polymerized polymeric material. Thus the aqueous phase always retains its integrity. By emulsifying or suspending the aqueous phase into the polymeric precursor materials, very small discrete "micro-compartments" (alternatively referred to as "droplets" or "cells") of the aqueous first phase can be formed in the polymeric second phase. Upon curing or crosslinking of the polymeric phase, these micro-compartments are fixed in dispersed positions which are essentially uniformly scattered throughout the polymeric material. An "emulsoid" of the aqueous first phase is thus formed in the polymeric second phase.

Preferably, the aqueous phase in this preferred embodiment is very evenly distributed within the polymeric phase, when it is fixed in position in the emulsoid, and its concentration is very evenly distributed throughout the emulsoid. As a result, the concentration of the aqueous phase is uniform through the emulsoid, and the sensing characteristics of the gas sensor of the invention are also very uniform.

Contrary to other gas sensors, by using very small emulsion sized particles, the surface area of the individual micro-compartments and thus the totality of the micro-compartments of the aqueous phase is very large. Because the surface area of the aqueous phase which is in contact with the surface area of the polymeric phase is very large for the gas sensors of this invention, gas exchange to the sensing aqueous phase is fast and is uniformly sensitive to the gas concentration within the polymeric phase.

A suitable homogenizer such as a Vertishear homogenizer may be used to emulsify the mixture of the aqueous phase and the polymeric precursor. The emulsification enhancement agents contribute to the stability of the emulsion or suspension such that it has an increased shelf life. When it is desired to form the gas sensor of the invention, the cross-linker and/or catalyst may be added (if they are not already present in the polymeric precursor) or the sensor may be exposed to visible light or UV light if a photosensitive initiator is present. The resulting mixture may then be shaped and cured.

A very simple gas sensor can be formed by simply depositing a drop of the mixture of the emulsion and a cross-linking agent onto the end of a fiber optic fiber and allowing it to cure into an emulsoid directly on the end of the fiber. Alternatively, the emulsion mixture or a sheet of sensor material formed from the emulsion as described in copending U.S. Patent application "Sensing Elements and Methods for Making Same," Ser. No. 08/159,799, now U.S. Pat. No. 5,508,509, can be placed in a sensor holder or "cassette" to form a sensor.

Following emulsification, the aqueous phase is present in the polymeric precursor in micro-compartments which are of a size less than 125 microns. Preferably the micro-compartments are nearly monodisperse and smaller than 5 microns. More preferably, gas sensors of the present invention will have micro-compartments of the aqueous phase in the polymeric phase wherein the majority of the population of the compartments will be on the order of 2 microns. It is, of course, realized that the particles will actually be in a statistical range of particle sizes, some slightly larger than the above noted sizes, some slightly smaller, depending on the emulsification procedure and apparatus.

The volume of the aqueous phase generally occupies between about 1 and 80% of the sensing composition. More preferably, the aqueous phase generally occupies between about 10 and 60% of the sensing composition, and most preferably between about 15 and 40% of the sensing composition.

The stability of the emulsion may be assessed by measuring the rheological properties of the emulsion as a function of time. The initial elastic or "storage" modulus of the uncured emulsion is generally greater than about 100 Pa and the equilibrium elastic modulus at 48 hours is also generally greater than 100 Pa when tested as described herein. More preferred emulsions have an initial elastic modulus greater than 200 Pa and an equilibrium elastic modulus at 48 hours greater than 200 Pa. Most preferred emulsions have an initial elastic modulus greater than 300 Pa and an equilibrium elastic modulus at 48 hours greater than 300 Pa.

At a minimum, the aqueous phase must contain an indicator of the gas of interest for which the sensor is being used. In general, the aqueous first phase includes a suitable indicator component or "dye" in a buffer solution. The first phase preferably also includes a water soluble emulsification enhancement agent such as a nonionic amphipathic surfactant.

Other materials can be incorporated into the aqueous phase microcompartments. Depending on the gas of interest, these other materials would be chosen to contribute to the operating characteristics of the gas sensor. For example, additional materials (e.g., humectants) can be added to lower the vapor pressure of the aqueous phase in the polymeric phase so as to retard the evaporation of the aqueous phase during formation of the gas sensor of interest. Aside from materials which contribute to the physical formation of the emulsoid of the aqueous phase in the polymeric phase, further additives can be added to the aqueous phase for enhancement of the storage and/or operating characteristics of the gas sensor as for instance osmoregulatory agents (e.g., NaCl) and/or bacteriostatic agents.

According to the present invention an indicator component or "dye" is utilized for sensing a gas of interest. Preferably, the indicator component is a pH sensitive optical indicator component. The dye can be one which acts with the gas of interest either by directly interacting with the gas or by indirectly acting with the gas, as for example, by sensing a pH change in a medium wherein the pH change is caused by interaction of the gas of interest with that medium. Interaction of the gas of interest with the dye, either directly or indirectly, can be monitored by any suitable optical technique as for instance by either fluorescence or by absorption.

A particular gas of interest for the gas sensor of this invention is carbon dioxide. Preferably for sensing carbon dioxide a pH sensitive dye would be solubilized in the aqueous phase. Gas exchange through the polymeric phase and into the aqueous phase solubilizes the carbon dioxide gas in the aqueous phase as carbonic acid which interacts with the buffer ions. The dye chosen is one which is responsive to the concentrations of the ionic species of the carbonic acid in the aqueous phase, i.e., an acid-base responsive dye.

In choosing a dye for measuring carbon dioxide in blood, consideration is given to matching the pKa of the dye to the pH range of the aqueous phase induced by physical $CO_2$ levels. In constructing a gas sensor of this invention for use in sensing carbon dioxide gas in blood, we have found that hydroxypyrene trisulfonate ("HPTS") has characteristics which are particularly desirable. HPTS, which is a known fluorescence dye for carbon dioxide, has a relatively large "Stokes shift." For use in fluorescence spectroscopy, this separates the excitation light from the emission light which improves the measurement of the emission light for improved gas sensor performance. The hydroxypyrene trisulfonic acid can be used as a free acid or as one of its salts as for instance an alkali or alkali earth salt.

Suitable indicator components for use in the present invention include: 9-amino-6-chloro-2-methoxyacridine; 2',7'-bis-(2-carboxyethyl)-5-(and-6)-carboxyfluorescein; 2',7'-bis-(2-carboxyethyl)-5-(and-6)-carboxyfluorescein, acetoxymethyl ester; 2',7'-bis-(2-carboxyethyl)-5-(and -6)-carboxyfluorescein, acetoxymethyl ester; 5-(and -6)-carboxy-2',7'-dichlorofluorescein; 5-(and-6)-carboxy-2',7'-dichlorofluorescein diacetate; 5-(and -6)-carboxy-4',5'-dimethylfluorescein; 5-(and -6)-carboxy-4',5'-dimethylfluorescein diacetate; 5-carboxyfluorescein; 6-carboxyfluorescein; 5-(and -6)carboxyfluorescein; 5-carboxyfluorescein diacetate; 6-carboxyfluorescein diacetate; 5-carboxyfluorescein diacetate, acetoxymethyl ester; 5-(and -6)-carboxyfluorescein diacetate; 5-(and -6)-carboxynaphthofluorescein; 5-(and -6)-carboxynaphthofluorescein diacetate; 5-(and -6)-carboxySNAFL®-1, succinimidyl ester {5'(and 6')-succinimidylester-3,10-dihydroxy-spiro[7H-benzo[c]xanthene-7,1'(3'H)-isobenzofuran]-3'-one}; 5-(and -6)-carboxySNAFL®-2, succinimidyl ester {5'(and 6')-succinimidylester-9-chloro-3,10-dihydroxy-spiro[7H-benzo[c]xanthene-7,1'(3'H)-isobenzofuran]-3'-one}; carboxySNAFL®1{5'(and 6')-carboxy-3,10-dihydroxy-spiro[7H-benzo[c]xanthene-7,1'(3'H)-isobenzofuran]-3'-one}; carboxySNAFL®-1 diacetate {5'(and 6')-carboxy-3,10-diacetoxy-spiro[7H-benzo[c]xanthene-7,1'(3'H)-isobenzofuranl]-3'-one}; carboxySNAFL®-2{5'(and 6')-carboxy-9-chloro-3,10-dihydroxy-spiro[7H-benzo[c]xanthene-7,1'(3'H)-isobenzofuran]-3'-one}; carboxySNAFL®-2 diacetate {5'(and 6')-carboxy-9-chloro-3,10-diacetoxy-spiro[7H-benzo[c]xanthene-7,1'(3'H)-isobenzofuran]-3'-one}; carboxySNARF®-1 {5'(and 6')-carboxy-10-dimethylamino-3-hydroxy-spiro[7H-benzo[c]xanthene-7,1'(3'H)-isobenzofuran]-3'-one}; carboxySNARF®-1, AM acetate {3-acetoxy-5'-acetoxymethoxycarbonyl-10-dimethylamino-spiro[7H-benzo[c]xanthene-7,1'(3'H)-isobenzofuran]-3'-one}; carboxySNARF®-2 {5'(and 6')-carboxy-10-diethylamino-3-hydroxy-spiro[7H-benzo[c]xanthene-7,1'(3'H)isobenzofuran]-3'-one}; carboxySNARF®-2, AM acetate {3-acetoxy-5'-acetoxymethoxycarbonyl-10-diethylamine-3-hydroxy-spiro[7H-benzo [c]xanthene-7,1'(3'H)-isobenzofuran]-3'-one}; carboxySNARF®-6 {5'(and 6')- carboxy-10-diethylamino-3-hydroxy-spiro[7H-benzo[c]xanthene-7,1'(3'H)-isobenzofuran]-3'-one}; carboxySNARF®-X {5'(and 6')-carboxy-3-hydroxy-tetrahydroquinolizino[1,9-hi]spiro[7H-benzo[c]xanthene-7,1'(3'H)-isobenzofuran]-3'-one}; 5-chloromethylfluorescein diacetate; 4-chloromethyl-7-hydroxycoumarin; Cl-NERF {4-[2-chloro-6-(ethylamino)-7-methyl-3-oxo-3H-xanthen-9-yl]-1,3-benzenedicarboxylic acid}; dextran, BCECF, 10,000 MW, anionic {dextran, 2',7'-bis(2-carboxyethyl)-5 (and 6)-carboxy-fluorescein, artionic}; dextran, BCECF, 40,000 MW, anionic; dextran, BCECF, 70,000 MW, anionic; dextran, Cl-NERF, 10,000 MW, avionic; dextran, Cl-NERF, 70,000 MW, anionic; dextran, Cl-NERF, 10,000 MW, artionic, lysine fixable; dextran, DM-NERF, 10,000 MW, anionic {dextran, 4-[2,7-dimethyl-6-(ethylamino)-3-oxo-3H-xanthen-9-yl]-1,3-benzene dicarboxylic acid, anionic}; dextran, DM-NERF, 70,000 MW, anionic; dextran, DM-NERF, 10,000 MW, anionic, lysine fixable; dextran, 7-hydroxycoumarin, 10,000 MW, neutral; dextran, 7-hydroxycoumarin, 70,000 MW, neutral; dextran, β-methylumbelliferone, 10,000 MW, neutral; dextran, β-methylumbelliferone, 70,000 MW, neutral; dextran, SNAFL®-2, 10,000 MW, anionic {dextran, 9-chloro-3,10-dihydroxy-spiro[7H-benzo[c]xanthene-7,1'(3'H)-isobenzofuran]3'-one, artionic}; dextran, SNAFL®-2, 70,000 MW, anionic {dextran, 10-dimethylamino-3-hydroxyspiro[7H-benzo[c]xanthene-7,1'(3'H)-isobenzofuran]-3'-one, anionic}; dextran, SNARF®-1, 10,000 MW, anionic; dextran, SNARF®-1, 70,000 MW, anionic; 1,4-dihydroxyphthalonitrile; DM-NERF {4-[2,7-dimethyl-6-ethylamino)-3-oxo-3H-xanthen-9-yl]1,3-benzene dicarboxylic acid}; fluorescein diacetate; 8-hydroxypyrene-1,3,6-trisulfonic acid, trisodium salt; naphthofluorescein; naphthofluorescein diacetate; SNAFL®-1 {3,10-dihydroxy-spiro[7H-benzo[c]xanthene-7,1'(3'H)-isobenzofuran]-3'-one}; and SNAFL®-1, diacetate {3,10-diacetoxy-spiro[7H-benzo[c]xanthene-7,1'(3'H)-isobenzofuran]-3'-one}. Many of the above indicator compounds are commercially available from Molecular Probes, Inc. "SNARF" and "SNAFL" are registered trademarks of Molecular Probes, Inc. The structures of many of the aforementioned indicator compounds are listed in "Handbook of Fluorescent Probes and Research Chemicals", 5th Edition, pages 129 to 141 (1992) by Richard P. Haugland, which is herein incorporated by reference. Also absorption dyes such as chlorophenol red, bromo cresol purple, nitrophenol, bromo thymol blue, pinachrome and phenol red could be used.

Preferably, the concentration of the dye in the aqueous phase would be from about 1 millimolar to about 20 millimolar with about a 2 to 8 millimolar solution being typically used.

Certain properties of the emulsion or suspension between the aqueous phase and the polymeric precursor can be enhanced by adding additional agents herein identified by the terminology "emulsification enhancement agents". These emulsification enhancement agents enhance certain manufacturing properties such as shelf life of the gas sensor intermediates by stabilizing the emulsion with respect to aggregation and coalescence. By stabilizing the emulsion or suspension of the aqueous phase and the polymeric precursor with respect to aggregation, it is not mandatory to immediately polymerize the aqueous phase-polymeric precursor emulsion or suspension into the emulsoid gas sensor of the invention. With the addition of the emulsification enhancement agents, the emulsion or suspension of the aqueous phase and polymeric precursor is stable and can be set aside for formation into the emulsoid gas sensor of the invention at a later time. This reduces the need to adhere to a tight manufacturing schedule and reduces or prevents the generation of manufacturing "scrap materials" which are economically wasteful.

We have discovered that a particularly preferred emulsification enhancement agent system comprises the combination of a water soluble emulsification enhancement agent and a water insoluble emulsification enhancement agent. The water soluble emulsification enhancement agent is preferably provided in the aqueous first phase and the water insoluble emulsification enhancement agent is preferably provided in the hydrophobic second phase.

Preferably, the water soluble emulsification enhancement agents are amphipathic copolymers or surfactants. More preferably, the water soluble emulsification enhancement agents are nonionic, amphipathic copolymers or surfactants.

In general, an amphipathic compound is a molecule capable of forming micelles and generally consists of a chemical structural group (the lyophobic group) having very little affinity for the solvent (hence low solubility in that solvent), combined with a chemical structural group (the lyophilic group) having very high affinity for the solvent (hence high solubility in that solvent). When the solvent is water or predominantly aqueous, the lyophobic group is described as hydrophobic and the lyophilic group is described as hydrophilic.

Preferred water soluble emulsification enhancement agents comprises a nonionic, amphipathic copolymer containing both hydrophilic and hydrophobic moieties. More preferably, the hydrophilic moiety is polyethylene oxide and the hydrophobic moiety is polypropylene oxide.

In one preferred embodiment, the water soluble emulsification enhancement agent is an ABA block copolymer, wherein the A block is a polyethylene oxide moiety and the B block is a polypropylene oxide moiety. Alternatively, the water soluble emulsification enhancement agent may be an AB, BA, or BAB block copolymer, wherein the A block is a polyethylene oxide moiety and the B block is a polypropylene oxide moiety.

Suitable water soluble emulsification enhancement agents have a "hydrophile-lipophile balance" (HLB) of at least 5, when determined as described herein. Preferred water soluble emulsification enhancement agents have a HLB of at least 7, more preferred water soluble emulsification enhancement agents have a HLB of at least 8, and most preferred water soluble emulsification enhancement agents have a HLB of at least 10.

Preferred sensors are formed from emulsions in which the water soluble emulsification enhancement agent has a "cloud point" greater than 20° C. More preferred sensors are formed from emulsions in which the water soluble emulsification enhancement agent has a "cloud point" greater than 60° C., and most preferably greater than 100° C.

Preferably, the water soluble emulsification enhancement agent is present in a concentration up to about 10 weight % in the sensing composition. More preferably, the water soluble emulsification enhancement agent is present in a concentration of between 0.01 and 5 weight % in the sensing composition, and most preferably, the water soluble emulsification enhancement agent is present in a concentration of between 0.1 and 3 weight % in the sensing composition.

Preferred water soluble emulsification enhancement agents include block copolymer surfactants such as "PLURONIC" and "PLURONIC R" surfactants from BASF (Wyandotte, Mich.). Suitable block copolymer surfactants are prepared by the controlled addition of propylene oxide to the two hydroxyl groups of propylene glycol. Ethylene oxide is then added to sandwich this hydrophobe between hydrophilic groups. The general structure of commercially available block copolymers of this type (PLURONIC) is represented below:

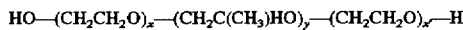
HO—(CH$_2$CH$_2$O)$_x$—(CH$_2$C(CH$_3$)HO)$_y$—(CH$_2$CH$_2$O)$_x$—H

Alternatively, copolymers may be prepared by reacting ethylene oxide with ethylene glycol. Propylene oxide is then added to obtain hydrophobic blocks on the outside of the molecule. The general structure of commercially available block copolymers of this type (PLURONIC R) is represented below:

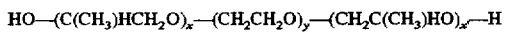
HO—(C(CH$_3$)HCH$_2$O)$_x$—(CH$_2$CH$_2$O)$_y$—(CH$_2$C(CH$_3$)HO)$_x$—H Suitable commercially available surfactants include ABA block copolymers such as PLURONIC surfactants, and BAB block copolymers such as Pluronic R surfactants. Suitable PLURONIC surfactants include: L10, L35, L42, L44, L62, L62D, L62LF, L63, L64, L72, L77, L92, F38, F68, F68LF, F77, F87, F88, F98, F108, F127, P65, P75, P84, P85, P103, P104, P105, and P123. PLURONIC F108 is presently most preferred. Suitable PLURONIC R surfactants include: 10R5, 10R8, 17R4, 17R8, 25R4, 25R5, 25R8, and 31R4.

Also suitable are similar ABA and BAB surfactants sold under the tradenames Poloxamers (BASF); Hodags (Calgene Chemical); and Synperonics (ICI Chemicals).

Other suitable water soluble emulsification enhancement agents include polyalkylene oxide-modified polydimethylsiloxane surfactants such as "SILWET" surfactants from OSi Specialties. In general, these block copolymer surfactants are composed of a siloxane molecular backbone with organic polyalkylene oxide pendant groups. A major class of these surfactants is a linear polydimethylsiloxane to which polyethers have been grafted through a hydrosilation reaction. The general structure of these surfactants is represented below:

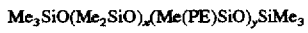
Me$_3$SiO(Me$_2$SiO)$_x$(Me(PE)SiO)$_y$SiMe$_3$ where:
PE is —CH$_2$CH$_2$CH$_2$O(EO)$_m$(PO)$_n$Z;
Me is methyl;
EO represents ethyleneoxy;
PO represents 1,2-propyleneoxy; and
Z can be either hydrogen or a lower alkyl radical.
Another class is a branched polydimethylsiloxane to which polyethers have been attached through condensation chemistry. These surfactants have the general structure:

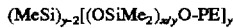
(MeSi)$_{y-2}$[(OSiMe$_2$)$_{x/y}$O-PE]$_y$ where:
PE is —(EO)$_m$(PO)$_n$R, and
R is a lower alkyl group.
By varying the coefficients x, y, m, and n, a broad range of surfactants are obtained.

Suitable SILWET surfactants include: L77, L720, L7001, L7002, L7087, L7200, L7230, L7600, L7604, L7605, L7607, and L7657.

Other suitable water soluble emulsification enhancement agents include block copolymer surfactants comprising propylene oxide and ethylene oxide blocks. The general structure of commercially available block copolymers of this type is represented below:

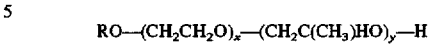
RO—(CH$_2$CH$_2$O)$_x$—(CH$_2$C(CH$_3$)HO)$_y$—H where:
R is H or alkyl.
Representative examples of surfactants of this class include: Hypermer B261 (PEO-PPO block copolymer), Dow P15-200 (random copolymer of PEO and PPO), and UCON 75H-90000 (random blocks of PEO and PPO).

Other suitable water soluble emulsification agents include nonionic surfactants based on ethylene oxide. The general structure of commercially available surfactants of this type is represented below:

R-(CH$_2$CH$_2$O)$_x$-H where:
R is H, OH, or alkyl, provided that x is at least 40, and preferably at least 70, when R is H or OH.
Representative examples of water soluble EEAs of this class where R is OH, include polyethylene oxide. Suitable polyoxyethylene alcohols also include BRIJ surfactants available from ZENECA, formerly available from ICI Chemicals, such as BRIJ 35, BRIJ 68, BRIJ 97, BRIJ 99, BRIJ 700 and BRIJ 700s. Representative examples of water soluble EEAs of this class where R is alkyl, include polyoxyethylene sorbitan fatty esters (e.g., polyoxyethylene sorbitan monolaurate, polyoxyethylene sorbitan monopalmitate, and polyoxyethylene sorbitan monostearate) such as TWEEN surfactants available from Zeneca. Suitable TWEEN surfactants include TWEEN 20 (polyoxyethylene (20) sorbitan monolaurate), TWEEN 40, TWEEN 60, and TWEEN 80.

Suitable water soluble emulsification enhancement agents have a weight average molecular weight between 100 and 50,000. Preferred water soluble emulsification enhancement agents have a weight average molecular weight between 500 and 20,000, and more preferred water soluble emulsification enhancement agents have a weight average molecular weight between 5,000 and 20,000.

The aqueous phase preferably includes a suitable buffer. For example, aqueous compositions can be prepared by addition of various amounts of indicator, sodium bicarbonate, and a 50:50 mix of monobasic sodium phosphate and dibasic sodium phosphate. Those skilled in the art will recognize that these same compositions can be prepared in alternate ways without affecting the resultant buffer composition or the resultant buffer performance as a function of CO$_2$ partial pressure. Furthermore, it is recognized that the sodium ion or chloride ion as counterions for the buffering species can be replaced by other salt forming ions without changing the scope or intent of this invention.

Preferred for use in sensing carbon dioxide is a bicarbonate ion based buffer in the aqueous phase. Such a buffer can be chosen so as to have a buffer range compatible with the response range of the dye. Such a range might, for instance, mimic the physiological pH range of blood. Suitable for the preparation of such a bicarbonate ion buffer would be sodium bicarbonate, sodium carbonate and sodium hydroxide or other suitable buffer agents. Suitable dispersed aqueous first phases are buffered to a pH range between about 5 and 14. For measuring blood carbon dioxide with hydroxypyrene trisulfonic acid, a pH range between about 7 and 8 is the most desirable.

Preferably, the concentration of the sodium bicarbonate and HPTS indicator should be chosen to optimize the sensitivity of the sensor over the range of $CO_2$ partial pressures commonly encountered during blood gas monitoring. In addition, this optimized sensitivity can be obtained at a higher sodium bicarbonate concentration by increasing the pKa of the indicator.

Generally the concentration of the phosphate buffer in the aqueous phase would be from about 1 millimolar to about 50 millimolar with about a 10 millimolar solution typically being used. Generally the concentration of the bicarbonate buffer in the aqueous phase would be from about 5 millimolar to about 200 millimolar, with about a 20 millimolar formal concentration being used.

The aqueous phase also preferably includes a suitable humectant. Although not contributing essentially to the stability of the emulsion, the addition of a humectant to the dispersed aqueous phase may add additional improvements to the cured emulsoid which include improved intensity stability in the dry coated web, improved rehydration rate, improved autoclave stability, and improved manufacturing robustness. In one embodiment, the humectant constitutes the major component of the dispersed phase.

Preferred humectants may provide sensors having a shorter equilibration time when the sensor is moved from a dry environment to a humid or aqueous environment compared to a sensor that does not contain a humectant. In addition, more preferred humectants are thermally stable at temperatures up to 121° C. for 1 hour.

In general, a humectant is a substance that has an affinity for water and provides a stabilizing action on the water content of a material or composition. Suitable humectants may vary in molecular weight, chemical composition, heat stability, and purity. Examples of preferred humectants include hydroxypropyl starch, hydroxyethyl starch, dextran, polyvinylalcohol, glycerol, polyvinylpyrrolidone, xanthan gum, gum arabic, methyl cellulose, tragacanth, acacia, agar, pectin, sodium alginate, alginate derivatives, proteins, gelatins, guar gum, polyethylene glycol, polyethylene oxide, and hydrogels.

Suitable commercially available humectants include: Starpol 530 (a hydroxypropyl-substituted polysaccharide with $M_w \sim 500,000$ to $600,000$), Starpol 560 (a hydroxypropyl-substituted polysaccharide with $M_w \sim 900,000$ and comprising a mixture of 27 parts amylose and 73 parts amylopectin), glycerol, trehalose, xanthan gum, etc.

Suitable humectants include water soluble molecules having a weight average molecular weight below about 4 million. Preferred humectants include water soluble molecules with a weight average molecular weight below 2 million, and more preferably those molecules having a weight average molecular weight below 1,000,000.

The amount of humectant in the sensor's dispersed phase is preferably chosen to provide the desired additional improvements to the emulsion. In one embodiment, the humectant is present in an amount between about 0.5 and 99% by weight of the dispersed phase. More preferably, for sensors used in a wet medium, such as blood, the humectant is present in an amount between 1 and 70% by weight of the dispersed phase, and most preferably, the humectant is present in an amount between 5 and 30% by weight of the dispersed phase. Preferably, for sensors used in a dry medium, such as air, the humectant is present in an amount at least 1% by weight of the dispersed phase, more preferably, the humectant is present in an amount at least 30% by weight of the dispersed phase, most preferably, the humectant is present in an amount at least 50% by weight of the dispersed phase, and optimally, the humectant is present in an amount at least 70% by weight of the dispersed phase.

A hydrophobic second phase (e.g., a polymeric phase) is chosen as a carrier for the dispersed aqueous phase and to maintain the individual micro-compartments of the first phase in their dispersed form. The second phase should be permeable to the gas of interest. It should also be translucent or transparent to the wavelength or wavelengths of light utilized in the measurement of the gas of interest. Further, since it is necessary to maintain the aqueous phase isolated from the carrier fluid of the gas of interest, the second phase should be substantially impermeable to liquid water. In order to isolate the indicator and/or any other ingredients in the aqueous phase, the hydrophobic phase should also be impermeable to ionic species.

Because of their high gas permeability and ionized hydrogen impermeability, silicone polymers are preferred for use as the hydrophobic secondary phase which separates the aqueous phase and the medium being analyzed. Care should be taken to select appropriate materials for use as the hydrophobic phase or to treat the materials to remove or immobilize any partitioning species that might contribute to undesirable drift.

In general, the polymeric phase can be prepared via several polymerization reactions. In addition to traditional "addition type" polymerization, the polymeric phase can be prepared using free radical polymerization reactions (e.g., using silicones having ethylenically unsaturated groups); condensation polymerization reactions (e.g., using silanol terminated silicones cross-linked with alkoxyl silanes using catalysts such as tin derivatives); or photoinitiated polymerization reactions (e.g., using ultraviolet or visible light catalysts).

In one presently preferred embodiment the polymeric phase is prepared via a photoinitiated polymerization reaction and optionally followed with a thermal polymerization reaction. This may be done using either UV, near IR, or visible light. In one embodiment a free-radical initiator is utilized to crosslink an acrylate or methacrylate functional silicone polymer. Alternatively, a radiation activated hydrosilation reaction may be employed (as described in U.S. Pat. Nos. 4,530,879, 4,510,094, and 4,916,169, which are herein incorporated by reference) with traditional siloxane polymers and crosslinkers.

For use in forming a carbon dioxide gas sensor, polydimethysiloxane, used in conjunction with a cross-linking agent and a platinum catalyst such as a Karstedt catalyst, is particularly preferred. Alternatively, a photo-activated catalyst, such as are described in U.S. Pat. Nos. 4,916,169; and 5,145,886, may be used and may result in a decrease in scrap and waste compared to typical silicone catalyst formulations. Photoactivated systems are also preferred for their greater flexibility in manufacturing. Traditional silicone systems require careful attention to working time and setting time constraints. Great care must be taken to fully form the sensor within the working time of the silicone material. Failure to finish forming the sensor within the allotted time results in scrap product. Photo-activated materials are more convenient, since the activation step can be delayed until the sensor is completely and fully formed. This virtually eliminates waste due to premature setting.

Suitable photoinitiators for use in the present invention should not undesirably contribute to $CO_2$ conditioning drift or undesirably interfere with the transmission of either the excitation light signal or the emission light signal through the sensor.

Preferably, from about 1 gram to about 4 grams of the aqueous solution would be added to about 10 grams of the polymeric precursor. More preferably, about 2 to 3 grams of the aqueous phase per 7 to 10 grams of the polymeric precursor is used. Preferably, the cross-linking agent would be added from about 2% to about 20% by weight of the polymeric precursor with approximately 5% to 10% by weight with respect to the weight of the polymeric precursor typically being used.

As previously mentioned, the hydrophobic phase preferably comprises a water insoluble emulsification enhancement agent. The water insoluble emulsification enhancement agent preferably comprises a plurality of dispersed hydrophobic particles. Such agents serve to stabilize the initially formed emulsion or dispersion prior to final crosslinking or cure. These agents, when added to the hydrophobic phase, may also serve to enhance the structural characteristics of the hydrophobic phase after crosslinking. That is to say, the filler may serve to improve the mechanical strength or integrity of the cured matrix.

While not wishing to be bound by any particular theory as to the mechanism, we believe that the amphipathic nature of the water soluble emulsifier allows the emulsifier to orient at the water/oil interface and interact with the water insoluble emulsifier which is also oriented at that interface, thus leading to enhanced aggregation stability.

Suitable hydrophobic particles include organic or inorganic particles. Suitable particles include hydrophilic particles that have been treated with an agent or agents to render the surface hydrophobic. Suitable inorganic particles include aluminum oxide, zirconium oxide, titanium oxide, and silica. Preferred inorganic particles are treated and include fumed, precipitated, or finely divided silicas.

More preferred inorganic particles include the colloidal silicas known under the tradenames of CAB-O-SIL (available from Cabot) and AEROSIL (available from Degussa).

Suitable inorganic fillers include surface treated colloidal silica fillers such as CAB-O-SIL TS-530, and TS-720; and Degussa R812; R812S, and R202. "CAB-O-SIL TS-530" is a high-purity treated fumed silica which has been treated with hexamethyldisilazane (HMDZ). The treatment replaces many of the hydroxyl groups on the fumed silica with trimethylsilyl groups. As a result the silica is made hydrophobic. The surface area of the TS-530 material is approximately 200 $m^2/g \pm 40$ $m^2/g$ (using BET method).

Preferably the hydrophobic filler particle has a relative hydrophobicity, as described and measured herein, of at least 2, more preferably at least 4, and most preferably at least 5.

Preferably the hydrophobic filler particle is a finely-divided, substantially water insoluble solid, with a mean volume average diameter less than 5 microns, the surface of which may be treated with an organic compound. Suitable filler particles exhibit a low affinity for water, as reflected by a solid/liquid contact angle (measured through the aqueous phase) of greater than 90 degrees. More preferred hydrophobic particles have a solid/liquid contact angle (measured through the aqueous phase) greater than 110 degrees, and most preferred hydrophobic particles have a solid/liquid contact angle greater than 130 degrees.

Preferably, the radius of curvature of the hydrophobic particle is less than the radius of curvature of the emulsion droplet. More preferred hydrophobic particles have a mean volume diameter less than 5 microns, and most preferred hydrophobic particles have mean volume diameter less than 1 micron.

In one embodiment, the hydrophobic particles are chemically bonded to the hydrophobic second phase. This may be accomplished, for example, by bonding the silicone chains to the silica in the presence of an ammonia catalyst under heat and vacuum. Alternatively, hexamethyldisilazane can be used.

Preferably, the filler is selected such that undesirable partitioning species are not inadvertently brought into the sensor composition. For example, Tullanox 500 fumed silica has been observed to contain a significant level of a basic species (introduced with a hydrophobic surface treatment). The residual base (believed to be ammonia) likely leaves the sensor during storage or during processing of the sensor. Nevertheless, as an extra precaution, one may preferably use filler which has been heated under vacuum (e.g., for 12 hours at 150° C. and at 2 mm Hg) or a deammoniated filler such as CAB-O-SIL TS-530. Also preferred are silica fillers which have been hydrophobically treated by processes which do not result in the presence of basic impurities (such as CAB-O-SIL TS 610 or CAB-O-SIL TS 720).

Preferably, the hydrophobic particles are present in a concentration of between 0.1 and 20 weight % in the sensing composition. More preferably, the hydrophobic particles are present in a concentration of between 1 and 10 weight % in the sensing composition, and most preferably between 3 and 6 weight % in the sensing compound.

Certain materials used in traditional $CO_2$ sensors, for example, in the aqueous first phase, in the hydrophobic second phase, or in other parts of the sensor, are believed to undesirably contribute to $CO_2$ conditioning drift and/or saline drift. These materials may themselves contribute to drift or contain "impurities" or residual species (hereinafter collectively referred to as "partitioning species") that contribute to the drift problem. The amount of such materials or impurities needed for drift to occur is extremely small. Because of the large number of ingredients and materials that go into a typical $CO_2$ sensor, titratable partitioning species are ubiquitous unless extraordinary precautions are taken to eliminate them or control them. Each and every part of the sensor must be considered for its potential contribution of titratable partitioning species. This includes the aqueous phase (including, for example, surfactants used therein), the hydrophobic phase (including, for example, the silicone polymer and/or cross-linker, and fillers used therein), any optional films or overcoats (for example, substrate films or webs used when coating sensing elements, optical barrier films, etc.), and any optional adhesives and/or adhesion promoters used to secure the sensor to an optical fiber, cassette, or a substrate film. The partitioning species may also be liberated or released from one or more of the sensor components as a result of a subsequent process (e.g., a heating process or autoclaving) or exposure to an environment. For example, some materials contained within traditional sensors contain species which are believed to become partitioning species only when the sensor is steam sterilized or heated. With this understanding of the causes of $CO_2$ conditioning drift and saline drift several methods are proposed to provide sensors which are essentially drift free. By careful selection and/or purification of components essentially drift-free sensing elements are provided which are not adversely affected by steam sterilization. A more complete discussion of the causes of $CO_2$ conditioning drift and saline drift is found in copending U.S. patent application Ser. No. 08/375,304, now U.S. Pat. No. 5,607,645.

Other particular gasses of interest for the gas sensor of this invention include ammonia, $SO_2$, and $NO_2$. For sensing ammonia, a pH sensitive dye would be solubilized in the aqueous phase. Gas exchange through the polymeric phase and into the aqueous phase solubilize the ammonia gas in the aqueous phase which interacts with the buffer ions. The dye chosen is one which is responsive to the concentrations of the ionic species of the ammonia in the aqueous phase, i.e., an acid-base responsive dye. Preferred for use in sensing ammonia is an ammonium chloride ion based buffer in the aqueous phase. Such a buffer can be chosen so as to have a buffer range compatible with the response range of the dye. Suitable indicators for use in measuring ammonium concentration include acridine orange, 1-hydroxypyrene-3,6,8-trisulphonate, and 1-naphthol-4-sulphonate.

In one embodiment, this invention is directed to a gas sensor which can be utilized with a fiber optical cable, i.e., a single optical fiber or a bundle of the same. Preferred sensors have a response time less than 5 minutes, more preferably less than 2 minutes, and most preferably less than 1 minute. The fiber optic cable is associated with appropriate optical and electronic devices for imposing an optical signal from the gas sensor. A plurality of techniques for transmitting and reading appropriate optical signals can be utilized with the gas sensors of the invention. The optics and electronics for gas sensing will not be reviewed in detail, reference being made to the disclosures of U.S. Pat. Nos. RE 31,879; 4,557,900; and 4,824,789, which are herein incorporated by reference. Notably, other means of transmitting light to and from the sensor may be employed. For example, a light source such as a LED may be placed next to or against the sensor.

In another embodiment, this invention is directed to a gas sensor comprising a sensor "cassette" through which a medium such as blood can flow. The cassette can be utilized with a fiber optical cable associated with appropriate optical and electronic devices, as discussed above, for imposing an optical signal from the gas sensor. U.S. Pat. Nos. 4,640,820 and 4,786,474 (Cooper) describe a suitable cassette, and are herein incorporated by reference. Notably, other means of transmitting light to and from the cassette may be employed. For example, a light source such as a LED may be placed next to or against the sensor or cassette.

Seen in FIG. 1 is a drop 10 of the emulsion or suspension of the aqueous phase in the polymeric precursor. As is evident, the micro-compartments 12 are dispersed in a uniform manner through the drop 10 of the emulsion.

Figure 2A:
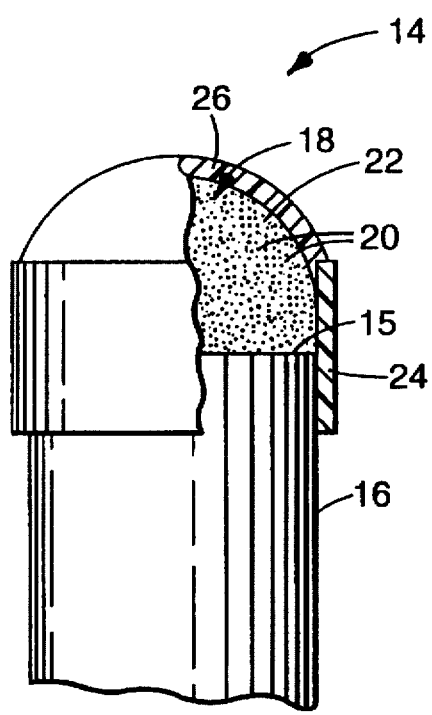
FIGS. 2a, 2b, 2c, and 2d are views in section of a gas sensor of the invention.
Figure 2A:

For formation of a very simple gas sensor 14 of this invention, in FIG. 2a, a drop of the above mixture is placed on the distal end 15 of an optical fiber 16. The mixture of the cross-linking agent and the polymeric precursor having the aqueous phase as an emulsion therein cures into an emulsoid 18 of the micro-compartments 20 of the aqueous phase in the polymeric material or carrier body 22. If desired, the emulsoid 18 can be retained on the end of the fiber 16 using a suitable optional sleeve 24. The sleeve 24 can be constructed from a suitable material such as Teflon or the like. Further, to avoid light intensity changes caused by factors other than the changes in partial pressure of the gas sensed, an overcoat 26 can be added as a layer over the exposed positions of the emulsoid 18. For use with a fluorescent dye, the overcoat 26 is chosen to be opaque to the excitation light wavelength $\lambda_{ex}$ and to the emission light wavelength $\lambda_{em}$ both of which are transmitted along the same single optical fiber 16. A suitable material for the overcoat 26 would be vinyl end-capped poly(dimethyl) siloxane impregnated with carbon black.

As is evident in FIG. 2a, the size of the gas sensor 14 is dictated only by the optical fiber size. The gas sensor 14 thus formed is of a sufficiently small size so as to be introducible directly into the cardiovascular system of a patient for direct real time measurement of the partial pressure of a blood gas such as carbon dioxide. If the fiber optic fiber 16 of FIG. 2a is typically about 125 micron in diameter, it is evident that the emulsoid 18 is approximately equal to or less than this size in each of its orthogonally oriented width, height and depth dimensions. Other constructions of gas sensors are also possible utilizing the emulsoid of this invention. It, of course, being realized that smaller sensors could be constructed by utilizing a smaller diameter fiber optic cable.

By using the above noted gas sensor construction in conjunction with HPTS as a pH sensitive dye, determination time of the carbon dioxide partial pressure is made in a time period of approximately one minute. This gas sensor preferably can be autoclaved to sterilize it without detracting from or degrading its performance and during its use it is essentially temperature stable.

Figure 2B:
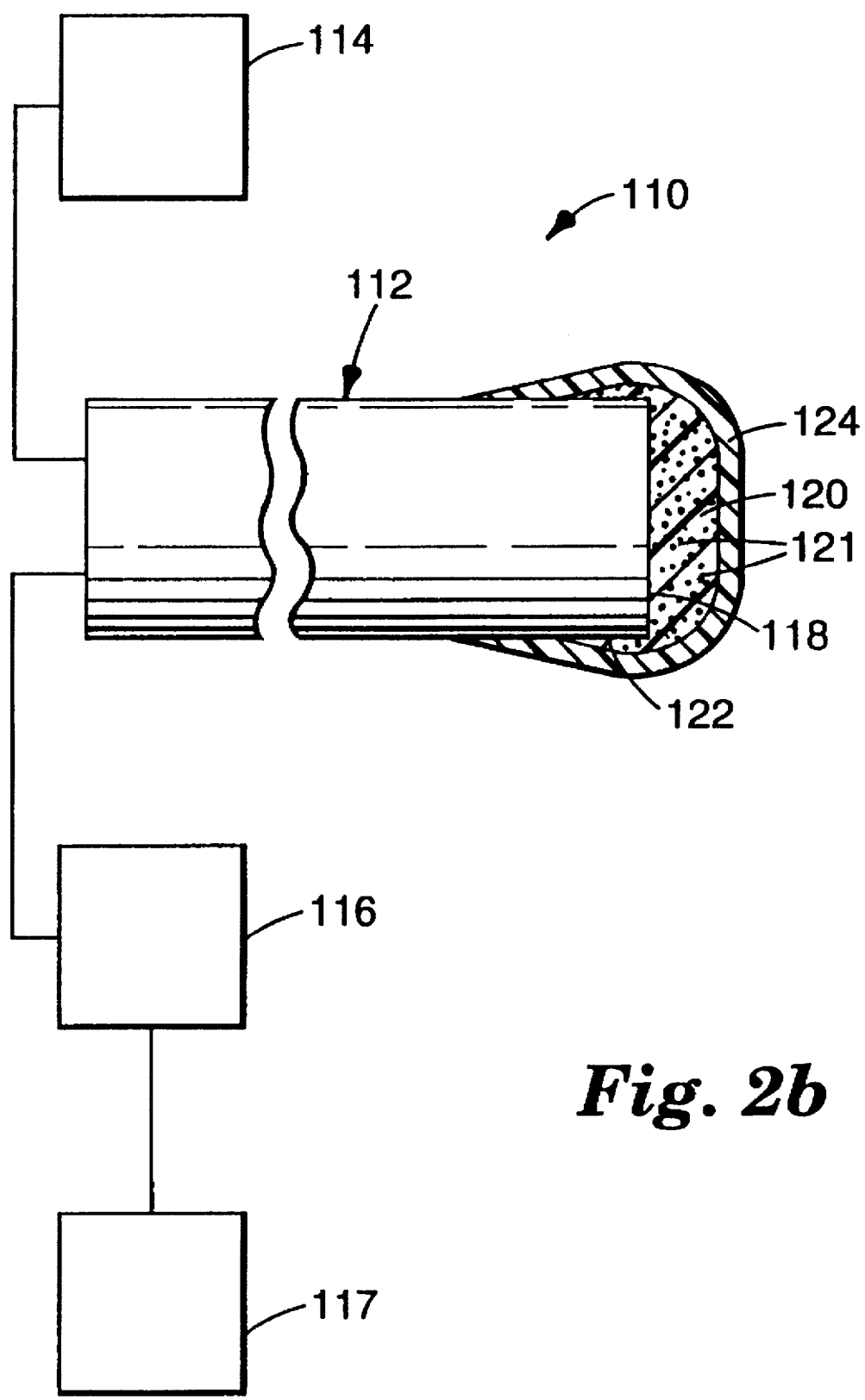

FIG. 2b shows a sensor 110 according to the present invention. Sensor 110 is adapted to determine the concentration or partial pressure of carbon dioxide in blood. An optical fiber 112 is connected to an appropriate light transmitting apparatus 114, which is capable of transmitting light at 410 and 460 nanometers. The light transmitting apparatus 114 generates the excitation light at these wavelengths. The optical fiber 112 is also connected to a light receiving apparatus 116, which, in turn, is connected to a conventional electronic processor 117. Located on the optical surface 118 of the optical fiber 112 is a matrix 120 which is a carbon dioxide permeable material, such as a cross-linked addition cured siloxane polymer. Within the matrix 120 is a plurality of micro-compartments 121 comprising an aqueous phase including HPTS indicator dye. The highly carbon dioxide permeable matrix 120 adheres to the optical surface 118 and slightly down along the sides 122 of the end of fiber 112. An opaque overcoat 124, comprising iron oxide pigment dispersed in an addition cured polysiloxane, can then be applied over the totality of the matrix 120 and down further along the side 122 of the fiber 112.

In use, sensor 110 functions as follows. The tip of optical fiber 112 including matrix 120 and overcoat 124 is exposed or immersed in blood, the carbon dioxide concentration of which is to be determined. Light transmitting apparatus 114 transmits light at 410 nanometers to the optical fiber 112. The excitation light at 410 nanometers causes the matrix 120 to fluoresce at 510 nm. In this case, the 410 nm light is absorbed primarily by the acidic form of HPTS. Excited state deprotonation follows, giving rise to 510 nm emission from the basic form of the dye. This emission is proportional to the amount of HPTS initially present in the acidic form. As the concentration of carbon dioxide in the blood increases, the pH of the aqueous phase drops and the intensity of 510 nm emission associated with 410 nm excitation increases. Light transmitting apparatus 114 then transmits light at 460 nm to the optical fiber. The excitation light at 460 nm also causes the matrix 120 to fluoresce at 510 nm. In this case, the 460 nm light is absorbed by the basic form of HPTS, which emits directly at 510 nm. This emission is proportional to the amount of dye initially present in the basic form. As the concentration of carbon dioxide in the blood increases, the intensity of 510 nm emission associated with the 460 nm excitation decreases. The fluorescent emitted signals are transmitted from matrix 120 through optical fiber 112 to light receiving apparatus 116. Processor 117 uses information received by light receiving apparatus 116 on the longer emitted signal to determine a value of the carbon dioxide concentration in the blood. Receipt and analysis of this fluorescent light by light receiving apparatus 116 and processor 117 may be carded-out in a manner similar to that described in U.S. Pat. Nos. RE 31,897 and 4,557,900. Processor 117 uses information received by light receiving apparatus 116 of the fluorescent signals emitted at 510 nanometers to develop a ratio of the emitted fluorescent signal associated with 460 nm excitation to the fluorescent signal associated with 410 nm excitation. Using this ratio together with the above-noted carbon dioxide concentration, processor 117 can determine a corrected concentration of carbon dioxide in the blood to be analyzed. This corrected carbon dioxide concentration is found to be accurate even if the optical fiber 112 is bent at one or more points along its length and/or if other light transmission difficulties are encountered.

The above-noted procedure may occur periodically or even substantially continuously to give substantially continuous carbon dioxide concentration results. Of course, the transmission of the excitation at 460 nanometers can take place before transmission of the excitation at 410 nanometers. Also, by proper selection of the optical indicators, e.g., fluorescent dyes, the concentration of other components of interest can be determined. In addition, media other than blood can be analyzed.

The optical fiber 112 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in U.S. Pat. No. 4,557,900, to provide extra corporeal monitoring of carbon dioxide concentration in the blood.

Figure 2C:
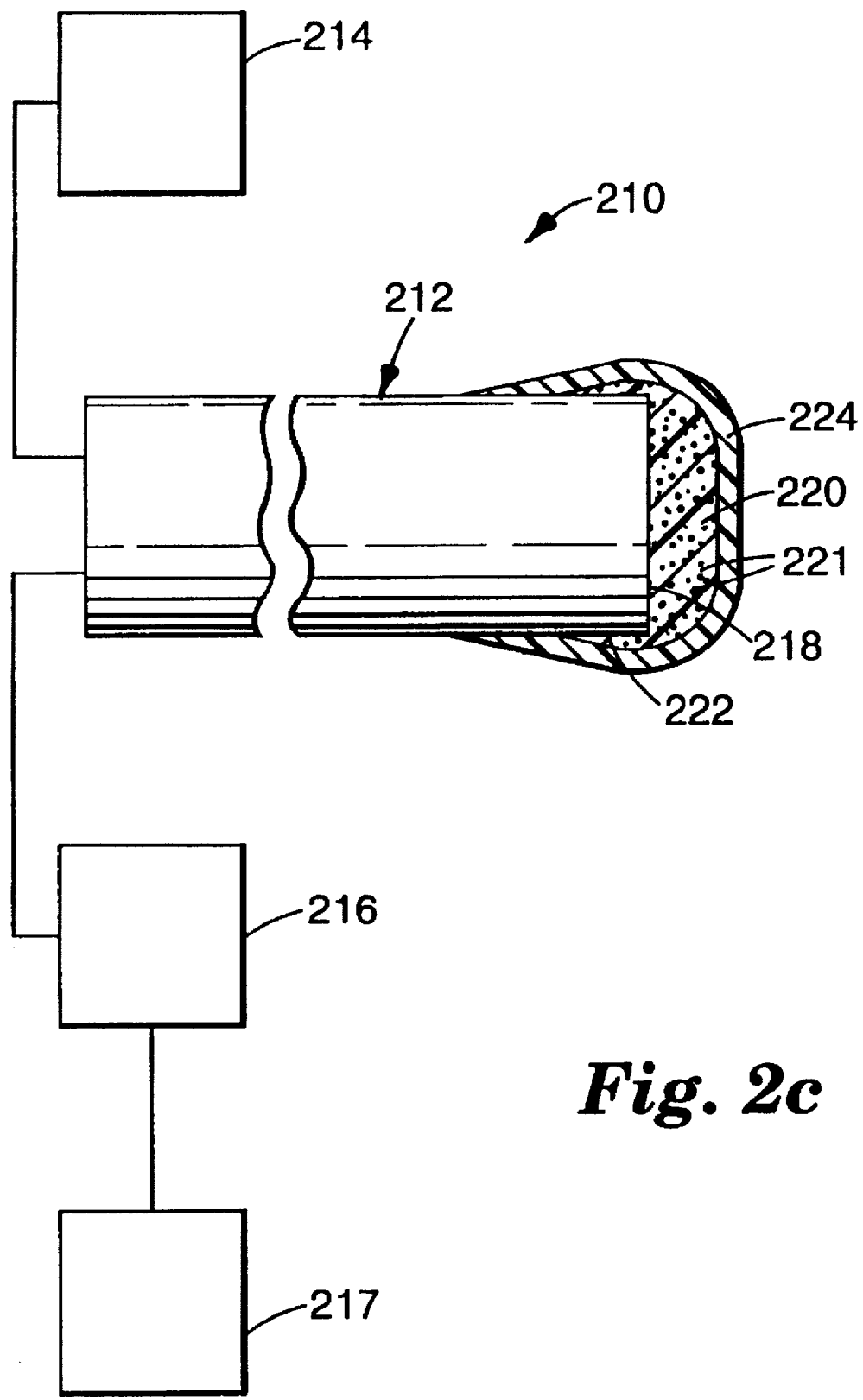

FIG. 2c shows a sensor 210 according to the present invention. Sensor 210 is adapted to determine the concentration or partial pressure of carbon dioxide in blood. An optical fiber 212 is connected to an appropriate light transmitting apparatus 214, which is capable of transmitting light at 543 nanometers. The light transmitting apparatus 214 generates the excitation light at this wavelength. The optical fiber 212 is also connected to a light receiving apparatus 216, which, in turn, is connected to a conventional electronic processor 217. Located on the optical surface 218 of the optical fiber 212 is a matrix 220 which is an carbon dioxide permeable material, such as a cross-linked addition cured siloxane polymer. Within the matrix 220 is a plurality of micro-compartments 221 comprising an aqueous phase including a dye (e.g., SNARF-6). The highly carbon dioxide permeable matrix 220 adheres to the optical surface 218 and slightly down along the sides 222 of the end of fiber 212. An opaque overcoating 224, comprising iron oxide pigment dispersed in an addition cured polysiloxane, can then be applied over the totality of the matrix 220 and down further along the side 222 of the fiber 212.

In use, sensor 210 functions as follows. The tip of optical fiber 212 including matrix 220 and overcoating 224 is exposed or immersed in blood, the carbon dioxide concentration of which is to be determined. Light transmitting apparatus 214 transmits light at 543 nanometers to the optical fiber 212. The excitation light at 543 nanometers causes the matrix 220 to fluoresce at two separate wavelengths. The emission at the shorter wavelength is associated with the acidic form of the indicator. The emission at the longer wavelength is associated with the basic form of the indicator. As the concentration of carbon dioxide in the blood increases, the pH of the aqueous compartment drops and the intensity of the short wavelength emission increases while the intensity of the long wavelength emission drops. Typically, the short wavelength emission is measured at 580 nm and the longer wavelength emission is measured at 630 mm. Both the emissions at 580 nanometers and 630 nanometers are dependent on the concentration of carbon dioxide in the blood. The fluorescent emitted signals are transmitted from matrix 220 through optical fiber 212 to light receiving apparatus 216. Processor 217 uses information received by light receiving apparatus 216 on the shorter emitted signal to determine a value of the carbon dioxide concentration in the blood. Receipt and analysis of this fluorescent light by light receiving apparatus 216 and processor 217 may be carded out in a manner similar to that described in U.S. Pat. Nos. RE 31,897 and 4,557,900. Processor 217 uses information received by light receiving apparatus 216 of the fluorescent signal emitted at 580 nanometers to develop a ratio of the emitted fluorescent signal at 580 nanometers to the fluorescent signal at 630 nanometers. Using this ratio together with the above-noted carbon dioxide concentration, processor 217 can determine a corrected concentration of carbon dioxide in the blood to be analyzed. This corrected carbon dioxide concentration is found to be accurate even if the optical fiber 212 is bent at one or more points along its length and/or if other light transmission difficulties are encountered.

The above-noted procedure may occur periodically or even substantially continuously to give substantially continuous carbon dioxide concentration results. Of course, the detection of the emission at 580 nanometers can take place before detection of the emission at 630 nanometers. Also, by proper selection of the optical indicators, e.g., fluorescent dyes, the concentration of other components of interest can be determined. In addition, media other than blood can be analyzed.

The optical fiber 212 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in U.S. Pat. Nos. 4,557,900, 4,640,820, and 4,786,474, to provide extra corporeal monitoring of carbon dioxide concentration in the blood.

Figure 2D:
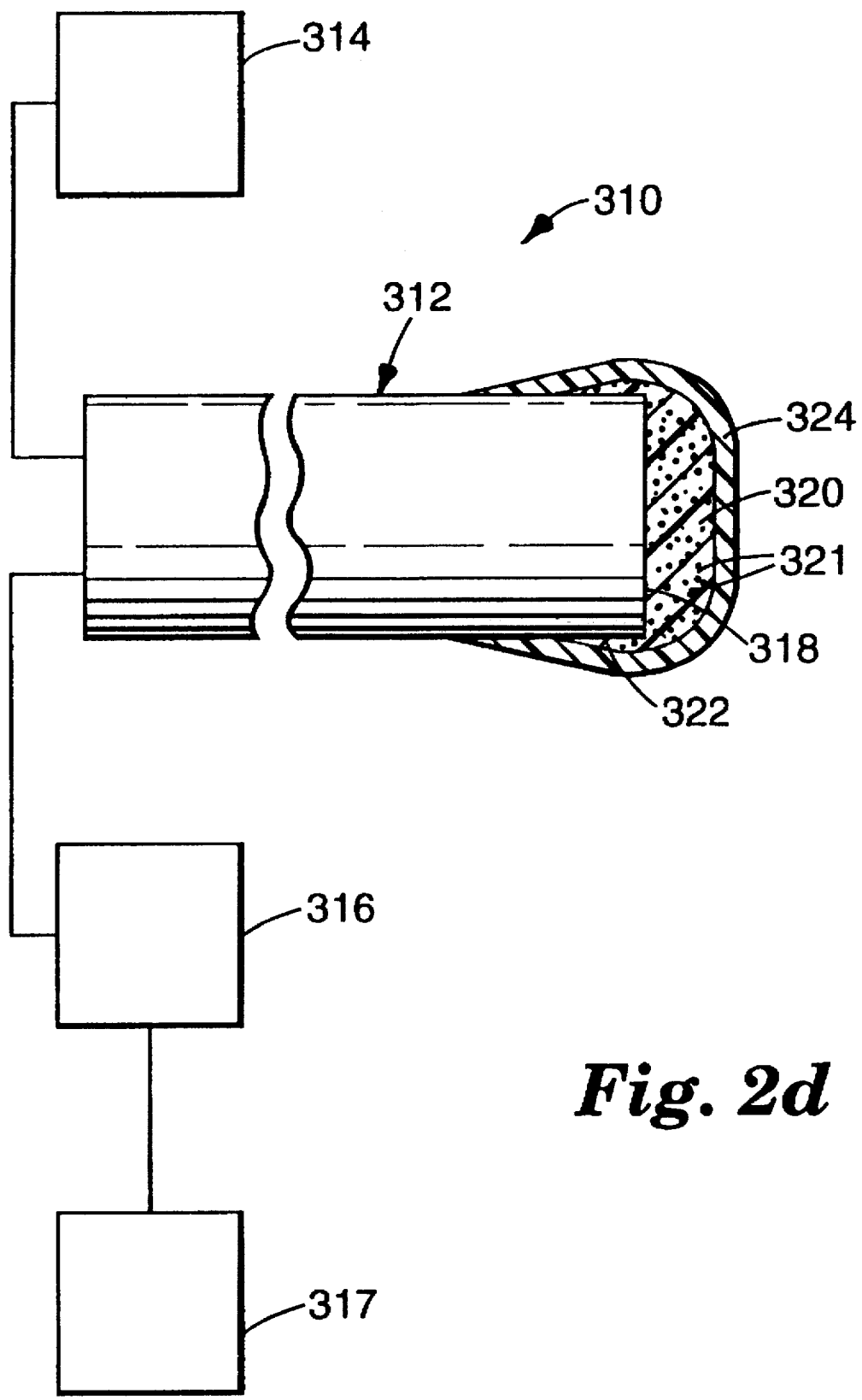

An alternate embodiment, which is described with reference to FIG. 2d, involves a sensor apparatus making use of intensity modulated (sine wave) signals in the MHz range. In this embodiment, sensor 310 is adapted to determine the concentration or partial pressure of carbon dioxide in blood. An optical fiber 312 is connected to an appropriate light transmitting apparatus 314, which is capable of transmitting intensity modulated (sine wave) light in the MHz range. The light transmitting apparatus 3 14 generates the modulated excitation light at this frequency. The optical fiber 312 is also connected to a light receiving apparatus 316, which, in turn, is connected to a conventional electronic processor 317. The light transmitting apparatus 314 includes a frequency generator (one or more frequencies simultaneously) linked to an electrically controlled light emitting structure, such as a light emitting diode, a frequency doubled light emitting diode, or a combination of elements such as a continuous wave laser or incandescent light source coupled to an acoustooptic modulator or electrooptic modulator, and the like. The light receiving apparatus 316 includes a highly sensitive light detector having a rapid response time. Suitable detectors include photomultiplier tubes such as those sold under the trademark R928 by Hamamatsu Photonics K.K., Hamamatsu, Japan, as well as avalanche photodiodes and microchannel plates, also available from the same supplier. Using techniques well known in the art, heterodyne detection can be implemented by modulating the detector sensitivity at a frequency, equal to the fundamental modulation frequency, $F_f$ in the MHz regime, plus or minus a heterodyne modulation frequency $F_h$ in the Hz or kHz region. The processor 317 may include, for example, an analog to digital converter coupled by a direct memory access device to a computer, or an analog phase comparator circuit known to those skilled in the art, and the like. The SLM 48000MHF Fourier Transform Spectrofluorometer manufactured by SLM-Aminco in conjunction with a HeNe laser provides frequency modulated light generation, light receiving apparatus and processor capability to perform the methods outlined herein; to measure phase shifts, demodulation factors, or both at either a single modulation frequency or simultaneously at several modulation frequencies. Commercial software is available to apply a well-known digital fast Fourier transform to the data and to interpret phase and demodulation data at multiple modulation frequencies in terms of a distribution of emission lifetimes and relative contributions.

Located on the optical surface 318 of the optical fiber 312 is a matrix 320 which is an carbon dioxide permeable material, such as a cross-linked addition cured siloxane polymer which is similar to the polymer described previously and containing a plurality of micro-compartments 321 comprising an aqueous phase comprising, for example, SNARF-6 dye (or any other suitable lifetime based pH indicator). The highly oxygen permeable matrix 320 adheres to the optical surface 318 and slightly down along the sides 322 of the end of fiber 312. An opaque overcoating 324, comprising iron oxide pigment dispersed in an addition cured polysiloxane, can then be applied over the totality of the matrix 320 and down further along the side 322 of the fiber 312.

In use, sensor 3 10 functions as follows. The tip of optical fiber 312 including matrix 320 and overcoating 324 is exposed or immersed in blood, the carbon dioxide concentration of which is to be determined. Light transmitting apparatus 314 transits light at 50 MHz and 543 nm to the optical fiber 312. This excitation light causes the matrix 320 to fluoresce at 610 nm, an isobestic point for emission from the acid and base forms of SNARF-6. The fluorescent emission is sine wave modulated. The emission lifetime for the acidic form of the dye is longer than the emission lifetime of the basic form of the dye. As the concentration of carbon dioxide in the blood increases, the pH of the aqueous compartment drops and the phase shift increases while the demodulation factor decreases.

The fluorescent emitted signal is transmitted from matrix 320 through optical fiber 312 to light receiving apparatus 316. Processor 317 uses information received by light receiving apparatus 3 16 on the emitted signal to determine the extent of the phase shift and/or the demodulation factor of this emitted signal. The extent of this phase shift and/or this demodulation factor is dependent on the concentration of carbon dioxide in the blood. Thus, by determining the extent of this phase shift and/or this demodulation factor, values of the carbon dioxide concentration in the blood can be obtained. Transmission, receipt and analysis of this modulated signal by light transmitting apparatus 314, light receiving apparatus 316 and processor 317 may be carded out using equipment and in a manner similar to that described in U.S. Pat. No. 4,840,485, which is incorporated herein by reference.

The above-noted procedure may occur periodically or even substantially continuously to give substantially continuous carbon dioxide concentration results. Of course, by proper selection of the optical indicators, e.g., fluorescent dyes, the concentration of other components of interest can be determined. In addition, media other than blood can be analyzed.

The optical fiber 312 may be in the form of a probe or a catheter insertable into a blood vessel of a patient to provide continuous on-line in vivo monitoring. Alternately, the present sensor can be embodied in a flow-through housing as shown, for example, in the above-referenced Heitzmann patent, to provide extra corporeal monitoring. In addition, the light transmitting apparatus 314 and/or light receiving apparatus 316 may be embodied in the flow-through housing without an intermediate optical fiber.

Figure 3:
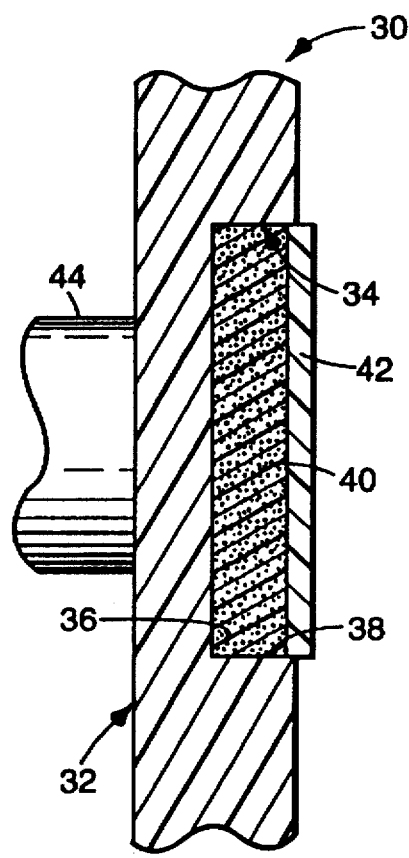
FIG. 3 is a partial view in section of a gas sensor of the present invention which comprises a flow through cassette comprising a sensing element.
Figure 4:
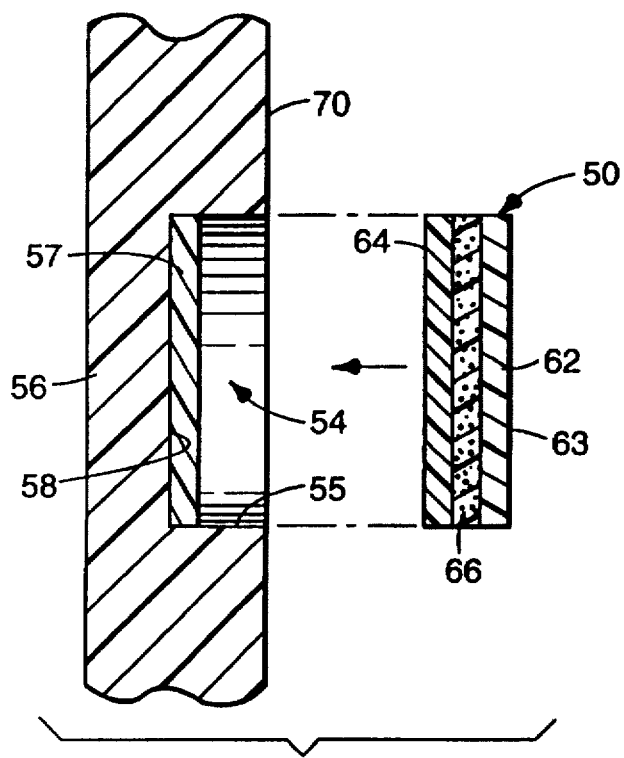
FIGS. 4 and 5 are two partial views in section of a gas sensor of the present invention which comprise a flow through cassette comprising a preformed laminate sheet sensing element.
Figure 5:
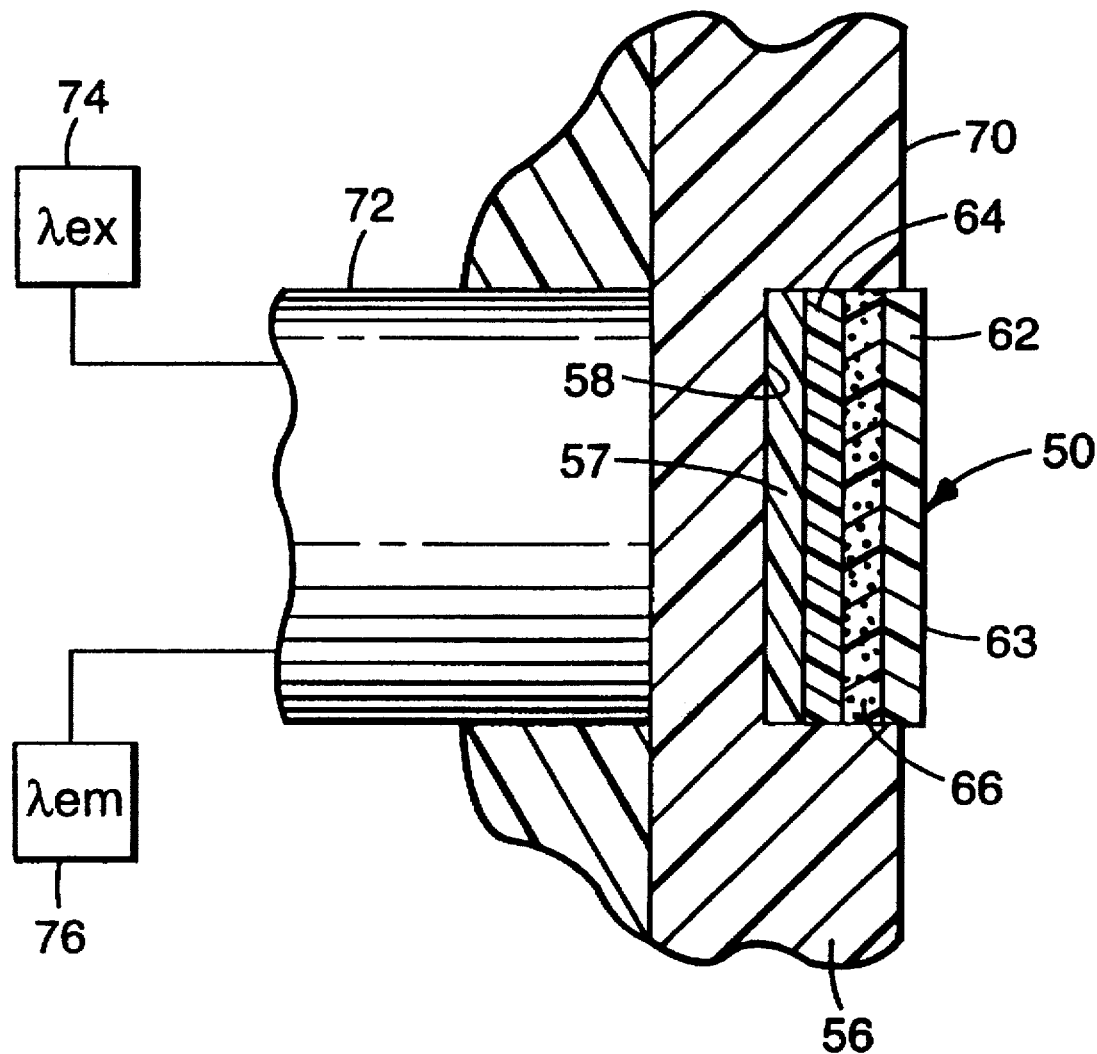

Seen in FIG. 3 is a schematic representation of an alternative $CO_2$ sensor of the present invention. In this embodiment the gas sensor 30 comprises a "cassette" or sensor holder 32 having a well 34. The well 34 is open at one end, includes a bottom end wall 36 and a side wall 38. A drop of emulsion 10 is placed in the well 34' and cured to form an emulsoid 40. An opaque layer 42 can be added as a layer over the exposed positions of the emulsoid 40. In operation, a medium such as blood is brought in contact with the exposed position of the emulsoid 40 (or alternatively in contact with the opaque layer 42). An excitation signal is transmitted through an optical fiber 44 which causes an emission signal from the indicator component. Alternatively, instead of using an optical fiber 44 to transmit the excitation and emission signals, one might either directly embed an LED and/or photodetector in the cassette or place an LED and/or photodetector in contact with the cassette (not shown). FIGS. 4 and 5 illustrate the use of a sensing element which may be produced as described in U.S. Pat. application Ser. No. 08/159,799, now U.S. Pat. No. 5,508,509, which is herein incorporated by reference.

As shown in FIG. 4, this individual sensing element 50 is placed into well 54 containing a transparent, silicone-based adhesive 57. Well 54 is open at one end, includes a right circular cylindrical side wall 55 and a circular bottom end wall 58. The size of well 54 is such that the individual sensing element 50 and silicone-based adhesive layer 57 completely fill the well. Individual sensing element 50 is placed in well 54 so that the transparent web layer 64 faces the bottom end wall 58 of well 54. The opaque layer 62 includes an exposed surface 63 which is raised relative to the inner surface 70 of sensor holder 56. The opaque layer 62 substantially shields sensing composition layer 66 from direct contact with the medium, e.g., blood, to be monitored. Depending on the specific sensing application involved, the exposed surface of the opaque layer can be recessed relative to, or flush with, the inner surface of the sensor holder.

Referring now to FIG. 5, in use sensor holder 56, made of a transparent polycarbonate material, is placed in abutting relation to optical fiber 72. Optical fiber 72 provides excitation light of appropriate wavelength from light transmitting apparatus 74 to excite the sensing component in the sensing composition layer 66 to fluoresce and provide a signal characteristic of the concentration of carbon dioxide located in the medium in contact with the opaque film 62. This optical fiber 72 also transmits the signal which is emitted from the sensing component and passes such signal to a light receiving apparatus 76, which processes or analyzes this emitted signal, e.g., as described in U.S. Pat. No. RE31,879, 4,557,900, and/or copending U.S. pat. application Ser. Nos. 08/136,967 and 08/137,289, now U.S. Pat. Nos. 5,462,879 and 5,409,666 respectively, to determine the concentration of carbon dioxide in this medium.

Methods for Assessing Emulsion Stability

Various methods have been used for assessing the stability of emulsions, as reviewed by Tadros and Vincent (*Encyclopedia of Emulsion Technology*, Vol. 1, P. Becher, Ed., New York, 1983, pp. 129–285). Preferred methods for assessing the stability of concentrated emulsions include microscope examination and rheological characterization of the emulsion as a function of time after homogenization.

The microscopic structure of emulsions was determined using a Zeiss standard 14 microscope with an Illuminator 100 halogen lamp/mercury/xenon and fluorescence source. The microscope was equipped with a Zeiss MC 63 camera, a calibrated 10× eye piece, and 16× and 40× objectives. Thin smears of emulsion samples were made on glass slides and mounted with a coverslip. The initial size distribution of emulsion droplets was noted and optionally recorded photographically.

Emulsion stability over a 48 hour period was quantified by measuring the dynamic viscoelastic properties of the emulsion using a Bohlin VOR controlled strain rheometer as described by Tadros (*Colloids & Surfaces, Physiochemical and Engineering Aspects*, 91 (1994) pp 50–55). Dynamic measurements as a function of time are often used to characterize emulsion stability because this method uses low strains and is therefore nondestructive. In this case, initial, 24 hour and 48 hour values of the elastic or "storage" modulus (G') and complex viscosity ($\eta^*$) were measured. In general, stable emulsions are characterized by high elastic modulus (greater than 100 Pa). Stability is further reflected by little or no percentage change in elastic modulus with time.

Prepared samples (3 ml) were carefully loaded into a concentric cylinder geometry with a cup diameter of 16.5 mm and a bob diameter of 14 mm which results in a gap of 1.25 mm. To minimize wall slip effects a serrated bob was used in these measurements. An 11 gcm or 40 gcm torque bar was used. All emulsions were subjected to an initial strain sweep at 0.001 to 0.20 radians (at 20 Hz) to help eliminate prior shear and loading effects on the emulsion microstructure. After the initial strain sweep a recovery time of 300 s was given to allow for equilibration. Then a strain sweep from 0.0005 to 0.20 radians (in 30 logarithmically spaced steps) at 20 Hz was performed and the data analyzed. The strain sweeps indicate a linear viscoelastic region over which the elastic modulus, G', is constant with strain. At higher strains the elastic modulus decreases with increasing strain. The elastic modulus values in the plateau (constant) region are averaged and reported.

A similar protocol is used in determining and averaging the complex viscosity. Using the initial strain sweep and a 300 second delay time gives good reproducibility of strain sweep measurements. Reproducibility on the same emulsion was shown to be ±7%. The measurements are performed in a darkened environment due to the fluorescent dyes incorporated in the droplets. Solvent evaporation losses were negligible over the 20 minute time period of a measurement; therefore a solvent trap was not used in these studies.

Methods for Assessing Hydrophobicity of the Colloidal Emulsifier

Various methods for determining the wetting characteristics of finely divided solids have been reviewed by Kaya and Koishi (KONA, No. 6, pp. 86–97, 1988). The preferred method for characterizing the wettability of hydrophobized silica surfaces is infrared spectroscopy, as taught by Flinn et al. (Flinn, D. H., Guzonas, D. A. and R. H. Yoon, *Colloids & Surfaces A: Physicochemical & Engineering Aspects*, 87, pp. 163–167, 1994).

Infrared spectra of particle emulsifiers were obtained by diffuse reflectance infrared Fourier transform spectroscopy (DRIFTS) using a Specac DRIFTS accessory in a Nicolet Magna 750 FT-IR spectrometer. The amount of sample relative to the amount of ground KBr in the sample cell was adjusted to obtain an absorbance of approximately 1 for the silica samples and approximately 1.5 for the polyethylene powders. The internal reference for the silica samples was calculated by taking the peak area of the $CH_3$ stretch at 2964 $cm^{-1}$ and dividing it by the peak area of an SiO band at 800 $cm^{-1}$ and then multiplying by 100. We define this as the relative hydrophobicity index.

Autoclaving

Sensors were autoclaved in loosely capped Pyrex jars containing carbonate buffer (10.3 mM $Na_2CO_3$ buffer and 144 mM NaCl) using a liquid cycle at 121° C. for 1 hour. The temperature was verified using an Omega 871 Digital Thermomoter with a Type K thermocouple (NiCr-NiAl) submerged in a Pyrex jar containing an equal volume of distilled water. These tests simulated sterilization conditions for a sensor product. A 3M "ATTEST" Steam Pack 1276 containing ATTEST 1262 Bacillus Stearothermophilis biological indicator may be used to validate the effectiveness of the sterilization cycle.

Sensor Performance Testing

The robustness of sensors was evaluated by measuring sensor intensity and response to $CO_2$. Sensors were excited at approximately 465 nm and the emission at 520 nm was measured using a xenon lamp in conjunction with an appropriate filter. Calibration slopes were determined by measuring the average intensities at 37° C. in buffer solutions tonometered with 2.8% and 8.4% $CO_2$. Measurements on individual sensors were reported as the average of 25 data points. Intensities were also measured at room temperature in air-sparged carbonate buffer ($I_{air}$) and after exposure to 0.5% w/v ammonia solution in deionized water ($I_{max}$), the latter measurement of total dye concentration in the sensor permitting sensor intensities to be normalized.

The following examples are offered to aid in the understanding of the present invention and are not to be construed as limiting the scope thereof. Unless otherwise indicated, all parts and percentages are by weight except that $CO_2$ gas compositions are expressed by volume percent or in terms of partial pressure in mm Hg.

EXAMPLES

Preparatory Example 1

Preparation of Stock Solutions

Various sensor emulsions were prepared by dispersing a water soluble aqueous phase (Stock A) and a hydrophobic emulsifier into a silicone continuous phase (Stock B).

To form an emulsion, 30 parts Stock A was mixed with 67 parts Stock B and 3 parts of a water insoluble emulsification enhancement agent. The water in oil emulsion was formed by homogenizing for 20 minutes at 25,000 rpm on a Vertishear Cyclone/Tempest IQ homogenizer (available from the Vertis Company) with macro blade assembly with cooling in an ice water bath. Care was taken to keep the emulsion out of the light.

Stock A was prepared by dissolving a water soluble emulsifier and optional humectants into a solution containing a fluorescent dye and optional buffers and osmolytes. The mixture was then placed into a foil wrapped jar and shaken on a mechanical shaker overnight.

In the working examples, Stock A was composed of 2.7 mM HPTS (8-hydroxy-1,3,6-pyrene trisulfonic acid, trisodium salt—available from Eastman Kodak); 8.1 mM $Na_2CO_3$; and 144 mM NaCl. In a preferred embodiment, Stock A also contained 5% Starpol 530 (hydroxypropyl-substituted polysaccharide—available from A. E. Staley Manufacturing Company, $M_w$ ~500,000 to 600,000, $M_n$ ~80,000 to 90,000) and 5% Pluronic F108 (polyethylene oxide-polypropylene oxide-polyethylene oxide block copolymer—available from BASF) added as the humectant and water soluble emulsification enhancement agent, respectively.

Stock B was composed of Dow Corning (designated as "DC") 7690 silicone with 5% DC 7678 crosslinker. In a preferred embodiment, the water insoluble emulsification enhancement agent was CAB-O-SIL TS-530 fumed silica, available from Cabot Corp., Billerica, Mass. (3% based on the weight of the entire sensor composition).

Three different mixing methods are exemplified. In mixing method #1, silica was added to Stock A and Stock B and homogenized together using a Vertishear Cyclone Tempest IQ for 20 minutes at 25,000 rpm. In mixing method #2, the hydrophobic emulsifier was first added to Stock B and dispersed at 5000 rpm for 5 minutes on the Vertishear in an ice water bath prior to adding to Stock A and homogenizing for 20 minutes at 25,000 rpm. In still other examples where either no silica was used or where the silica was already incorporated into the commercial silicone, no additional filler was added before Stock A and B were homogenized at 25,000 rpm for 20 minutes (mixing method #3). In the case of Example 8, Runs 3–5, the emulsion was sonicated in an ultrasonic bath during homogenization.

In order to form the cured sensors, a UV activated catalyst (cyclopentadienyl trimethyl platinum) was added in toluene and mixed by hand to give a final concentration of 0.02% in the final emulsion. Sensor emulsions were degassed at room temperature in a vacuum chamber, and then precision coated onto a polycarbonate web having a thickness of 0.018 cm (available from Miles, Inc.) primed with an adhesion enhancement component derived from a mixture containing water, 1.25% colloidal silica particles, 0.11% aminopropyltriethoxysilane, 0.5% ammonium hydroxide and 0.03% of a surfactant sold by Rohm and Haas under the trademark Triton X-100. Emulsions were precision coated using a notch bar coater or a coating apparatus sold by Hirano under the trademark M-200. Emulsions were cured under UV light for 2 minutes followed by optional heat curing at 70° C. for 3 minutes. Coating thickness was measured with a gage (Federal) to 0.0003 cm.

An opaque fill precursor (Stock C) was overcoated onto the cured silicone sensor. Stock C was composed of a dispersion of carbon black (Regal 99R—available from Cabot) in a poly(dimethyl)siloxane matrix (PLY-7501—available from NuSil Silicone Technology) having platinum catalyst (Cat-50—available from NuSil Silicone Technology), and polymerization inhibitor (XL 119—available from NuSil Silicone Technology). Stock C was precision coated as described above and cured at 70° C. for 2 minutes.

Alternatively, sensors were handcast directly onto an injection molded polycarbonate cassette at a thickness of 0.008 cm and UV cured. Sensors cassettes were hydrated in buffer containing 10.3 mM $Na_2CO_3$, and 144 mM NaCl buffer for 1 day at room temperature before testing.

Example 1

Presently Preferred Sensor Emulsion

This example illustrates the improvement of the invention relative to the state of the art with respect to lot-to-lot consistency and emulsion stability. As shown in Table 1a, 9 g of Stock A (comprised of 5% Staley Starpol 530 and 5% BASF Pluronic F108 in a 2.7 mM HPTS, 8.1 mM $Na_2CO_3$, and 144 mM NaCl solution) was added to 22 g Stock B (comprised of silicones DC 7690 and DC 7678) and 0.9 g (3%) water insoluble emulsification enhancement agent (in this example labeled "Filler") and mixed by method #1, as described above.

TABLE 1a

| | Composition of sensor | | | | |
|---|---|---|---|---|---|
| | Stock A | | | | |
| Run # | Humectant | Water soluble emulsification enhancement agent | Stock B | Filler | Mixing Method |
| 1 | 5% Starpol 530 | 5% Pluronic F108 | DC7690/7678 | 3% TS-530 | 1 |

The stability of uncured sensors emulsions is summarized in Table 1b, as determined by visual observations of inital droplet size homogeneity and dynamic rheological measurements over the course of 48 hours.

TABLE 1b

| | Performance of Sensors Emulsions | | | | |
|---|---|---|---|---|---|
| | Visual | | Rheology | | |
| Run # | observations on emulsion | Initial droplet size (microns) | G' (Pa) (initial) | G' (Pa) (at 48 hrs) | % Change |
| 1a | Emulsion is viscous, not pourable | 1–2 monodisperse | 557 | 493 | –11.5 |
| 1b | Emulsion is viscous, not pourable | 2–4 monodisperse | 463 | 448 | –3.2 |
| 1c | Emulsion is viscous, not pourable | 2–4 monodisperse | 371 | 333 | –10.2 |

Referring to Table 1b, the uncured sensor emulsions showed uniformly small and monodisperse droplet sizes in the range of 1 to 4 microns. For all 3 replicates, the initial dynamic modulus was greater than 100 Pa, as would be expected by the visual appearance of the emulsions, which appeared viscous and not pourable. The modulus changed much less than 25% over 48 hours, indicating good aggregation stability for these emulsions. No visual change in droplet size was observed after 2 days. In addition, the viscosity of Run 1 was optimal for precision coating.

The sensor emulsion was precision coated and UV cured, according to the methods previously described. The performance of coated and cured sensors are recorded in Table 1c for pre- and post-autoclaved sensors.

TABLE 1c

| | Sensor performance | | | | |
|---|---|---|---|---|---|
| | Pre-autoclave | | Post autoclave | | Pre- | Post |
| Run # | $I_{air}$ | $I_{air}/I_{air}'$ | $I_{air}$ | $I_{air}/I_{max}$ | autoclave slope (mm$^{-1}$) | autoclave slope (mm$^{-1}$) |
| 1 | 24,957 | .97 | 21,358 | .92 | 0.018 | 0.017 |

The intensities of the sensors in air-sparged buffer ($I_{air}$) were greater than 20,000 counts, as would expected from a measurement of the maximum dye intensity ($I_{max}$) for a robust, stable sensor. Furthermore, the $I_{air}$ intensities were reproducible and stable to autoclave ($I_{air}/I_{max}>0.9$), with no acidification of the sensor occurring. Calibration slopes also were stable to autoclaving. The stability of the sensor intensities and calibration slopes pre- and post-autoclave is advantageous because consistent, reproducible and sterilization-insensitive calibration response is a requirement for transparently calibrated sensors.

Example 2

Various sensor formulations using emulsification methods known in the art were prepared and compared to sensor formulations of the present invention. The formulations and performance characteristics are summarized in Tables 2a, 2b, and 2c.

Run 1 illustrates that the presence of a humectant does not appear to be essential in promoting the stability of the gas sensing emulsion. Example 2, Run 1 was prepared identically to Example 1, Run 1 except without the humectant (Starpol 530) in Stock A. The emulsion shows a drop in G' of only 20% after 48 hours, indicating comparable stability relative to Example 1, Run 1 (with the humectant).

Comparative Run 2 corresponds to a gas sensor emulsion prepared without added emulsifiers, as would be exemplified by AVL patent EP 0 105 870. The method used to prepare Comparative Run 2 differed from EP 0 105 870 in that DC7690/7678 silicones were used rather than the Wacker Chemie silicones SLM40060/40061 listed in the AVL patent since the Wacker silicones are not presently commercially available. Homogenization conditions also differed. The emulsion was homogenized at 25,000 rpm for 5 minutes instead of the 30 seconds with a "high speed mixer" (at unspecified speed) listed in the AVL patent. The Stock A was formulated according to the AVL patent. The performance of the sensor emulsion is recorded in Table 2b. The emulsion was significantly less stable than the emulsion of Example 1, Run 1. Unlike the Example 1, Run 1 emulsion, Comparative Run 2 was of very low viscosity and pourable, as evidence by the low value for G' (G'<<100 Pa). The emulsion droplet size of Comparative Run 2 was polydisperse at 2–8 microns. The emulsion of Comparative Run 2 was handcast into sensors, as shown in Table 2c. Compared to Example 1, Run 1, Comparative Run 2 showed significantly lower intensities with a small $I_{air}/I_{max}$ and also exhibited greater variability in post-autoclave intensity.

Comparative Run 3 illustrates emulsion performance using a conventional low HLB surfactant as an emulsifier. Such emulsifiers may sometimes be predicted to yield stable water in oil systems. Pluronic L121 (HLB 0.5) was mixed into silicone Stock B at 5000 rpm for 5 minutes, prior to homogenization with Stock A at 25,000 rpm for 20 minutes using mixing method #3. Like Comparative Run 2, the emulsion showed very low viscosity and was visibly runny. The droplet size was polydisperse at 2–20 µm. The dispersed aqueous phase rapidly coalesced, making rheological measurements impossible. Stability was significantly poorer than the emulsion of Example 1, Run 1 or Example 2, Run 1.

In Comparative Run 4, an emulsion was prepared with a hydrophobic, colloidal emulsifier (CAB-O-SIL TS-530 fumed silica), but with no water soluble emulsification enhancement agent. Hydrophobic particles may sometimes act to stabilize water in oil emulsions. However, as shown in Table 2b, the resulting emulsion exhibited low viscosity and was polydisperse (2–30 micron droplet size). Coalescence was visible, resulting in rapid phase separation. Rheology measurements could not be made due to the poor stability of this emulsion. Because of poor emulsion stability, neither Comparative Runs 3 or 4 could be coated and cured to form emulsion sensors.

Comparative Run 5 illustrates yet another method of preparing an emulsion sensor composition using a high molecular weight, water soluble emulsifier added to the aqueous phase, as exemplified in U.S. Pat. No. 5,219,527 and European Patent Application 0 597 566 A1 (Puritan-Bennett Corporation). The emulsion was prepared by adding poly(vinylpyrrolidone) (PVP, 40,000 Da) to the aqueous phase Stock A (containing 10 mM HPTS and 100 mM NaHCO$_3$) and emulsifying with Stock B (containing Petrarch PS784 base silicone) at 25,000 rpm for 20 minutes. A portion of 10% PS123 crosslinker was added and mixed by hand. As shown in Table 2b, the emulsion was not viscous and the droplet size was still polydisperse (2–24 µm). The initial elastic modulus was 13.6 Pa, as would be expected for a low viscosity, pourable emulsion. The modulus showed a 28.7% drop after 48 hours, reflecting coalescence of the aqueous droplets, and gross phase separation was seen on standing. Upon precision coating, water droplets were observed to separate from the margins of the coating prior to curing. Handcast sensors were tested, as shown in Table 2d. The intensities were lower and more variable than in Example 1, Run 1. Intensities were reasonably stable to autoclave, however some intensity loss occurred.

Comparative Run 6 illustrates a sensor emulsion made with a high molecular weight amphiphilic emulsifier (dextran; 500,000 Da) and a silicone (DC 7690) filled with hydrophobic colloidal particles, prepared as described in U.S. Pat. No. 4,867,919 and U.S. patent application Ser. No. 08/137,289, now U.S. Pat. No. 5,409,666. In contrast to earlier Comparative Runs 2 to 5, the emulsion is viscous, with an initial elastic modulus greater than 100 Pa and a monodisperse droplet size (2–4 µm). Although the initial sensor intensities were comparable to those obtained in Example 1, Run 1, the intensity dropped precipitously by more than 70% post autoclave, to give $I_{air}/I_{max}$ approximately 0.27, indicating poor sterilization stability of the gas sensing composition.

Comparative Run 7 illustrates the critical role of hydrophobic colloidal emulsifier, working in conjunction with the amphipathic, water soluble emulsification enhancement agent, on the stability of the sensor emulsion. Comparative Run 7 was prepared in an identical method to Example 1, Run 1 except that no hydrophobic colloidal silica was added prior to homogenization. Contrary to Example 1, Run 1, which produced a stable water in oil emulsion of uniform droplet size, Comparative Run 7 yielded an unstable oil in water emulsion, having 20–40 micron oil droplets in a fluorescent aqueous continuous phase. The inversion of the water-in-oil emulsion to form an oil-in-water emulsion was also reflected by the extremely high values of the elastic modulus. Because the emulsion inverted, it had no utility as a gas sensor and no sensor was prepared.

TABLE 2a

Composition of sensors

| | Stock A | | | | |
|---|---|---|---|---|---|
| Run # | Humectant | Water soluble emulsification enchancement agent | Stock B | Filler | Mixing Method |
| 1 | none | 5% Pluronic F108 | DC7690/7678 | 3% TS-530 | 1 |
| C2 | none | none | DC7690/7678 | none | 3 |
| C3 | 5% Starpol 530 | 5% Pluronic L121 | DC7690/7678 | none | 3 |
| C4 | 5% Starpol 530 | none | DC7690/7678 | 3% TS-530 | 1 |
| C5[1] | none | 10% PVP (40,000) | PS784/PS123 | none | 3 |
| C6 | none | 33% Dextran (500,000) | DC7690/7678 | none | 3 |
| C7 | 5% Starpol 530 | 5% Pluronic F108 | DC7690/7678 | none | 1 |

[1]Homogenization time was 5 minutes at 25,000 rpm using the Vertishear.

TABLE 2b

Performance of Sensor Emulsions

| | | | Rheology | | |
|---|---|---|---|---|---|
| Run # | Visual observations on emulsion | Initial droplet size (microns) | G' (Pa) (initial) | G' (Pa) (at 48 hrs) | % Change |
| 1 | Emulsion was well mixed, viscous and not pourable. | 2–12 microns Polydispersed | 743 | 594 | −20.1 |
| C2 | Emulsion was well mixed, but low viscosity (pourable) | 2–4 microns with occasional 6–8 micron droplets | 2.3 | 2.5[1] | 8.7 |
| C3 | Emulsion was well mixed, but low viscosity and runny | Polydispersed at 2–20 microns with coalescence | failed[2] | failed | failed |
| C4 | Water droplets seen on side of jar and water phase visibly separates when jar is inverted. | Polydisperse at 2–30 microns and coalescence seen. | failed | failed | failed |
| C5 | Emulsion is not viscous (is pourable) and water separates at margins of coating. | Polydispersed at 2–24 microns with many at 16 microns. | 13.6 | 12.3 | −28.7 |
| C6 | Emulsion was viscous (not pourable). | 2–4 microns monodispersed | 104.6 | 32.6 | −68.8 |
| C7 | Emulsion was well mixed, viscous and not pourable. | Difficult to see individual fluorescent droplets. Large dark oil droplets of 20–40 microns seen. Inversion. | 829 | 1,650 | +99.0% |

[1]G' values were taken at 24 hours rather than 48 hours for this sample. The low G' values show that this sample is primarily viscous in nature.
[2]"Failed" denotes emulsion was too unstable to permit rheological characterization.

TABLE 2c

| | Sensor performance | | | |
|---|---|---|---|---|
| | Pre-autoclave | | Post autoclave | |
| Run # | $I_{air}$ | $I_{air}/I_{max}$ | $I_{air}$ | $I_{air}/I_{max}$ |
| C2[1] | 2506 | .27 | 1384 | .25 |
| C5 | 12581 | .98 | 8985 | .97 |
| C6 | 23684 | .90 | 6877 | .27[2] |

[1]Comparative example 2 was formulated without buffer as described in the AVL patent.
[2]These data are for a dextran emulsion prepared with PE 1055 silicones (as described in U.S. Pat. No. 4,867,919).

The preceding examples illustrate the improvements in stability and sensor performance obtained when a hydrophilic amphipathic emulsifier is used in conjunction with hydrophobic colloidal emulsifier in a water in oil emulsion based blood gas sensor. These improvements include shelf life stability of the emulsion for precision coating, autoclave stability, dry web stability, rapid rehydration, and transparent calibration through coating uniformity and intensity stability.

While not wishing to be bound by any particular explanation of mechanism, we believe that the these improvements result from the synergistic interaction of the two emulsifiers at the water-oil interface. As will be shown in the following examples, this synergistic effect is not limited to one particular chemical class of materials. Other amphipathic water soluble emulsification enhancement agents used with other hydrophobic colloidal emulsifiers known to those skilled in the art could be used in conjunction with a variety of suitable hydrophobic continuous phases to achieve similar performance improvements.

Example 3

Effect of Silicone Type on Sensor Emulsion Stability

This example illustrates that a wide range of hydrophobic continuous phases can be used in conjunction with this novel emulsification system.

Run 1 is the same formulation illustrated in Example 1. Run 1 and uses Dow Corning 7690 base silicone and DC 7678 crosslinker. These emulsions both show good stability as judged by the monodisperse droplet size and small change in G' over 2 days.

Similar results were obtained for a system using Nusil PLY7500 silicone as Stock B (Run 2). The emulsion shows a monodisperse droplet size of 2–4 microns and an initial G' of 518 Pa, which changes by only −18% after 48 hours.

Run 3 was prepared as described in Run 2, but with hexamethyldisilazane (HMDZ) treated silica and mixing method #3. The emulsion had an initial $G^1$ of 159 Pa, which changes by only −3% after 48 hours.

Run 4 was prepared using Huls PE1055 silicone containing in situ treated hydrophobic fumed silica as Stock B. As shown in Table 3b, the emulsion shows monodisperse droplets (2–4 microns), an initial G' of 16,800 Pa, and a change in G' after 48 hours of only 14 percent. Although this illustrates an emulsion with excellent stability, it does not represent a preferred embodiment, as the high elasticity of this emulsion makes it difficult to precision coat with high uniformity.

All of the emulsions described in this example exhibited superior stability, and illustrate that a variety of different silicone materials may be selected for use as the hydrophobic continuous phase. These silicones represented a range of initial continuous phase viscosities of 4,000 to 50,000 cS.

TABLE 3a

Composition of sensors

| | Stock A | | | | |
|---|---|---|---|---|---|
| Run # | Humectant | Water soluble emulsification enhancement agent | Stock B | Filler | Mixing Method |
| 1 | 5% Starpol 530 | 5% Pluronic F108 | DC7690/7678 | 3% TS-530 | 1 |
| 2 | 5% Starpol 530 | 5% Pluronic F108 | Nusil PLY7500 | 3% TS-530 | 1 |
| 3 | 5% Starpol 530 | 5% Pluronic F108 | Nusil PLY7500 | HMDZ silica (treated in situ) | 3 |
| 4 | 5% Starpol 530 | 5% Pluronic F108 | Huls PE1055 | silica (treated in situ) | 3 |

TABLE 3b

Performance of Sensor Emulsions

| | | | Rheology | | |
|---|---|---|---|---|---|
| Run # | Visual observations on emulsion | Droplet size (microns) | G' (Pa) (initial) | G' (Pa) (48 hrs) | % Change |
| 1 | Emulsion is well mixed, viscous and not pourable. | 2–4 monodispersed | 371 | 333 | −10.2 |
| 2 | Emulsion is well mixed, viscous and not pourable. | 2–4 monodispersed | 518 | 423 | −18.3 |

TABLE 3b-continued

Performance of Sensor Emulsions

| Run # | Visual observations on emulsion | Droplet size (microns) | Rheology G' (Pa) (initial) | G' (Pa) (48 hrs) | % Change |
|---|---|---|---|---|---|
| 3 | Emulsion is well mixed, viscous and somewhat pourable. | 2–12 polydispersed | 159 | 154 | −3.1 |
| 4 | Emulsion is extremely viscous and can only be sheared for 10 min. | 2–4 monodispersed | 16,800 | 19,200 | 14.3 |

Example 4

Effect of Hydrophobicity of Hydrophobic Colloidal Emulsifier on Emulsion Stability This example illustrates the importance of the relative hydrophobicity of the hydrophobic colloidal emulsifier on the emulsion stability. Relative hydrophobicity was determined using the IR method described previously. Table 4a lists a variety of colloidal emulsifiers and their relative hydrophobicity.

Runs 1 to 5 illustrate the use of hydrophobically treated fumed silica where the relative hydrophobicity is greater than 2. All of these silicas were prepared by treating the base silica with a hydrophobic molecule that replaces or covers hydrophilic hydroxyl groups. Like the emulsion of Example 1, Run 1, these emulsions all exhibit an initial G' greater than 100 Pa and a change of G' after 48 hours of 25% or less. As shown in Table 4c, good pre- and post-autoclave intensities were seen for these formulations.

Comparative Run 6 illustrates the effect of using a hydrophilic colloidal emulsifier such as CAB-O-SIL M5 in conjunction with an amphipathic water soluble emulsification enhancement agent (e.g., Pluronic Fk108). CAB-O-SIL M5 fumed silica was mixed into silicone according to Method #2 and homogenized with the standard aqueous phase Stock A. As shown in Table 4b, the emulsion showed inversion as evidenced by dark, nonfluorescent oil droplets with a diameter of 4–18 microns in a fluorescent aqueous continuous phase. Sensors prepared from this emulsion showed low pre-autoclave intensity, as shown in Table 4c. Hydration of these sensors in carbonate buffer showed visible leaching of the fluorescent dye out of the emulsion, as would be expected for an oil in water emulsion in which the dye was not adequately immobilized in silicone. This resulted in a wide intensity variability, reflected in the unusual $I_{air}/I_{max}$ ratio of 6.78 (a mean of 3 replicates).

Comparative Runs 7 and 8 illustrate the use of a hydrophobically treated fumed silica (CAB-O-SIL TS-610 and Degussa R972, respectively) where the relative hydrophobicity is less than 2. In both cases these silicas were prepared by treating the base silica with dimethyldichlorosilane agents, a process that replaces surface hydrophilic hydroxyl groups with hydrophobic methyl groups thereby rendering the surface more hydrophobic. Both Comparative Runs 7 and 8 yielded water in oil emulsions of very low viscosity which rapidly phase separated, as detected visually. No rheology or sensor performance measurements could be made due to this rapid phase separation of the dispersed aqueous phase.

TABLE 4a

Composition of sensors

| | Stock A | | | | | Relative hydropho- |
|---|---|---|---|---|---|---|
| Run # | Humectant | Water soluble EEA | Stock B | Filler | Mixing Method | bicity (IR) |
| 1 | 5% Starpol 530 | 5% Pluronic F108 | DC7690/7678 | 3% Cabosil TS-530 | 1 | 9.67 |
| 2 | 5% Starpol 530 | 5% Pluronic F108 | DC7690/7678 | 3% Degussa R812 | 1 | 5.65 |
| 3 | 5% Starpol 530 | 5% Pluronic F108 | DC7690/7678 | 3% Degussa R812S | 1 | 6.93 |
| 4 | 5% Starpol 530 | 5% Pluronic F108 | DC7690/7678 | 1.6% Cabosil TS-720 | 2 | 9.58 |
| 5 | 5% Starpol 530 | 5% Pluronic F108 | DC7690/7678 | 3% Degussa R202 | 1 | 11.1 |
| C6 | 5% Starpol 530 | 5% Pluronic F108 | DC7690/7678 | 3% Cabosil M5 | 2 | 0 |
| C7 | 5% Starpol 530 | 5% Pluronic F108 | DC7690/7678 | 3% Cabosil TS610 | 2 | 1.70 |
| C8 | 5% Starpol 530 | 5% Pluronic F108 | DC7690/7678 | 3% Degussa R972 | 2 | 1.72 |

TABLE 4b

Performance of Sensor Emulsions

| Run # | Visual observations on emulsion | Droplet size (microns) | Rheology G' (Pa) (initial) | G' (Pa) (48 hrs) | % Change |
|---|---|---|---|---|---|
| 1 | Emulsion is well mixed, viscous and not pourable. | Monodispersed at 1–2 microns | 530 | 453 | −14.5 |
| 2 | Emulsion was well mixed, viscous and not pourable. | Monodispersed at 2–4 microns | 922 | 748 | −18.9 |
| 3 | Emulsion was well mixed, viscous and not pourable. | Fluorescent droplets are <2 microns | 537 | 452 | −15.8 |
| 4 | Emulsion is well mixed and pourable (not runny) | Polydispersed at 2–14 microns | 145 | 117 | −19.3 |
| 5 | Emulsion is well mixed, viscous and not pourable | Polydispersed at 2–6 microns | 556 | 415 | −25.4 |
| C6 | Emulsion was well mixed, viscous and not pourable. Inversion of emulsion observed. Storage buffer appears cloudy and fluorescent. | Individual droplets were not seen. Dark oil droplets of 4–18 microns seen under fluorescence. | failed | failed | failed |
| C7 | Emulsion has very low viscosity (pourable, runny) and is visibly phase separated. | Phase separated | failed | failed | failed |
| C8 | Emulsion has very low viscosity (pourable, runny) and is visibly phase separated | Phase separated | failed | failed | failed |

TABLE 4c

Sensor performance

| | Pre-autoclave | | Post autoclave | |
|---|---|---|---|---|
| Run # | $I_{air}$ | $I_{air}/I_{max}$ | $I_{air}$ | $I_{air}/I_{max}$ |
| 1 | 24,957 | .97 | 21,358 | .92 |
| 2 | 24,795 | .96 | 21,288 | .97 |
| 3 | — | — | — | — |
| 4 | 20,716 | .96 | 27,564 | .92 |
| 5 | — | — | — | — |
| C6 | 1,083 | 6.78 | — | — |
| C7 | — | — | — | — |
| C8 | — | — | — | — |

This example illustrates that the hydrophobic colloidal emulsifier preferably has a relative hydrophobicity (as defined by FT-IR) greater than 2. This relative hydrophobicity can be obtained through a variety of surface treatments and manufacturing processes, as evidenced by the results from several chemically distinct fumed silicas obtained from different suppliers using different manufacturing processes.

Comparative Example 5

Effect of Particle Size of Hydrophobic Colloidal Emulsifier on Sensor Emulsion Stability This example shows the effect of particle size of the hydrophobic emulsifier on the stability of the sensor emulsion. The stability of the sensor emulsion was examined using hydrophobic particle emulsifiers where the radius of curvature was comparable to or greater than the emulsion droplets. Referring to Table 5a, particles composed of hydrophobic polyethylene waxes (Allied Signal, Accumist B series) and a partially oxidized (less hydrophobic) polyethylene (Allied Signal, Accumist A) with primary particle size of 6 and 12 microns were used in sensor emulsions. In Run 4, a hydrophobic clay (NL Chemicals, Inc., Bentone SD-2) with a primary particle size of 20 microns was also evaluated. All of these systems immediately yielded visually unstable emulsions, indicating that the particles were unable to orient at the water/silicone interface due to their high radius of curvature and surface structure. This is in stark contrast to the emulsion of Example 1, Run 1, which contains a colloidal hydrophobic fumed silica having a primary particle size of approximately 50 nm.

TABLE 5a

Composition of sensors

| | Stock A | | | Filler | | |
|---|---|---|---|---|---|---|
| Run # | Humectant | Water soluble emulsification enhancement agent | Stock B | Particle | Size (microns) | Mixing Method |
| C1 | 5% Starpol 530 | 5% Pluronic F108 | DC7690/7678 | 3% Acumist A6 | 6 | 1 |
| C2 | 5% Starpol 530 | 5% Pluronic F108 | DC7690/7678 | 3% Acumist B6 | 6 | 2 |
| C3 | 5% Starpol 530 | 5% Pluronic F108 | DC7690/7678 | 3% Acurriist B12 | 12 | 2 |
| C4 | 5% Starpol 530 | 5% Pluronic F108 | DC7690/7678 | 3% Bentone SD-2 | 20 | 2 |

TABLE 5b

Performance of Sensor Emulsions

| | | | Rheology | | |
|---|---|---|---|---|---|
| Run # | Visual observations on emulsion | Initial droplet size (microns) | G' (Pa) (initial) | G' (Pa) (48 hrs) | % Change |
| C1 | Emulsion had a very low viscosity and was pourable. It was visibly phase separated with a clear oil layer on the top of the emulsion, and a grainy, yellow sediment separates on standing. | Polydisperse droplets of 1–10 micron were aggregated in nonfluorescent, clear oil. | failed | failed | failed |
| C2 | Emulsion was initially well mixed and had a low viscosity (pourable). It visibly phase separated and became grainy. | 2–14 micron polydispersed and flocculated droplets with fluorescent, phase separated region. | failed | failed | failed |
| C3 | Emulsion was viscous and not pourable. Cured sensors were non-fluorescent. | Difficult to assign a fluorescent droplet size; dark oil droplets of 10–100 micron. Inversion of emulsion. | failed | failed | failed |
| C4 | Emulsion was tan in color and grainy with clay particles separating on standing. | Droplets are polydisperse (2–40 micron) | failed | failed | failed |

Example 6

Effect of Water Soluble Emulsification Enhancement Agent Structure on Sensor Emulsion Stability This example demonstrates the effect of water soluble emulsification enhancement agent structure on the stability of the sensor emulsion for water soluble emulsification enhancement agents with a variety of structures and molecular weights. These runs illustrated the preferred characteristics (water solubility and amphipathic nature) and most preferred characteristics (high molecular weight, i.e., greater than 2,000 Da) of the water soluble emulsification enhancement agent.

Comparative Run 1 illustrates the use of a nonionic, low molecular weight, amphipathic, low HLB, water insoluble emulsifier (I.C.I. Span 85) added to stock A and used in conjunction with a hydrophobic colloidal emulsifier (CAB-O-SIL TS-530) in the silicone phase. As illustrated in Table 6b, this emulsion inverts to a silicone in water emulsion, yielding oil droplets of 10–20 microns in diameter dispersed in a fluorescent continuous phase. The effect of emulsion inversion on sensor performance, as illustrated in Table 6c, is to dramatically lower the sensor intensity post-autoclave. In addition, the resulting sensor intensities (pre- and post-autoclave) are not reproducible, indicating that the emulsification method is not sufficiently robust for manufacturing transparently calibrated sensors.

Comparative Run 2 illustrates the use of an ionic, water soluble, amphipathic, high HLB emulsifier (I.C.I. G3300) added to Stock A and used in conjunction with CAB-O-SIL TS-530 and Stock B. Upon mixing, the emulsion showed monodisperse droplets in the range 2–4 microns, but exhibited low viscosity and low elasticity (G'=83 Pa), leading to aggregation instability as reflected by a drop in G' of 41% after 48 hours.

Comparative Run 3 illustrates the use of a nonionic, water insoluble, non-amphipathic emulsifier (Dow Polyglycol P4000, a polypropylene oxide) added to Stock B, used in conjunction with a hydrophobic colloidal emulsifier (CAB- O-SIL TS-530). As shown in Table 6b, the emulsion grossly phase separated immediately after preparation. Comparative Runs 1 and 3 illustrate the effect of water solubility of the water soluble emulsification enhancement agent in promoting stability of the gas sensor emulsion, and in yielding blood gas sensing compositions which exhibit good intensity stability.

Comparative Run 4 and Runs 5–8 illustrate the use of nonionic, water soluble, non-amphipathic emulsifiers comprised of polyethylene oxide of varying molecular weights. As shown in Comparative Run 4, a low molecular weight polyethylene oxide (200 Da) imparts no stability to the emulsion, with phase separation seen immediately after preparation. Increasing the molecular weight of the water soluble emulsification enhancement agent from 3350–300,000 Da (Runs 5–8) imparts some stability to the initial emulsions, but does not appear to impart long term stability to the emulsion, as reflected by a decrease in G' after 48 hours of 41 to 56%. This is in contrast to the emulsion of Example 1, Run 1, which shows less than a 10% change in G' after 48 hours. More preferred water soluble emulsification enhancement agents have an amphipathic character and are effective in stabilizing the emulsion.

The benefits of amphipathic character of the water soluble emulsification enhancement agent is further illustrated by Run 9, which uses a nonionic, high molecular weight, water soluble non-amphipathic emulsifier (Dow Polygylcol P15-200) in Stock A in conjunction with CAB-O-SIL TS-530 and Stock B. The Dow P15-200, while not amphipathic, is a copolymer composed of polyethylene oxide and polypropylene oxide, and is thus chemically similar to the Pluronic F108 amphipathic water soluble emulsification enhancement agent used in Example 1, Run 1. Run 9 produced an emulsion with an initial droplet size which was polydisperse at 2–10 microns. The emulsion of Run 9 showed less stability than the emulsion of Ex. 1, Run 1, as reflected by a 47% drop in G' after 48 hours.

Yet another example which illustrates the importance of the amphipathic character of the water soluble emulsification enhancement agent is provided by Run 10. Run 10 makes use of a nonionic, high molecular weight, water soluble non-amphipathic copolymer (UCON 75H-90000) composed of random blocks of polyethylene oxide and polypropylene oxide. Although the emulsifier has a similar molecular weight and chemical composition to the most preferred water soluble emulsification enhancement agent illustrated in Ex. 1, Run 1, it is less effective in stabilizing the emulsion, yielding an initially polydisperse droplet distribution of 2–8 microns and a 64% drop in G' after 48 hours.

Comparative Run 4 and Runs 5 to 10 clearly illustrate the importance of the amphipathic character of the water soluble emulsification enhancement agent in enhancing long term emulsion stability. While not wishing to be bound by any particular theory as to the mechanism, we believe that the amphipathic nature of the emulsifier allows the water soluble emulsification enhancement agent to orient at the water/oil interface and interact with the hydrophobic colloidal emulsifier which is also oriented at that interfaced, thus leading to enhanced aggregation stability.

Run 11 illustrates the use of a nonionic, low molecular weight, water soluble, amphipathic, high HLB emulsifier (I.C.I. Tween 20) added to Stock A and used in conjunction with CAB-O-SIL TS-530. Although the emulsion initially showed monodisperse droplets in the range of 2–4 microns, the emulsion exhibited a 34% drop in G' after 48 hours. In addition, sensors fabricated from the emulsion of Run 11 delaminated during autoclaving. While not wishing to be bound by any particular theory, we believe that the delamination may have resulted from the migration of this relatively mobile, low molecular weight emulsifier during autoclaving. Although this is a suitable water soluble emulsification enhancement agent, it illustrates an additional benefit of using a higher molecular weight emulsification enhancement agent.

The following runs illustrate the more preferred approach of our invention, namely, the use of an amphipathic, hydrophilic water soluble emulsifier in conjunction with a water insoluble, hydrophobic colloidal particle emulsifier. The preferred emulsions show improved stability relative to emulsification methods known in the art. An additional advantage of our novel emulsification method is improved sensor intensity stability, particularly after autoclaving.

Run 12 illustrates a nonionic, intermediate molecular weight, water soluble, amphipathic, PEO-PPO block copolymer emulsifier (Hypermer B261). Although the resulting emulsion is initially polydisperse at 3–14 microns, the initial G' drops only 25% over 48 hours, indicating acceptable stability. In addition, sensors prepared from this emulsion show good intensity both before and after autoclaving as shown in Table 6c.

Run 13 shows the use of a nonionic, low molecular weight, water soluble, amphipathic (intermediate HLB) emulsifier (Silwet L77). The resulting emulsion exhibited an initial monodisperse droplet size of 2–4 microns, and stability as reflected by a drop in G' of only 6% after 48 hours. As shown in Table 6c, sensor intensities were acceptable both pre- and post-autoclave.

Run 14 is similar to the emulsion of Ex. 1, Run 1. This emulsion exhibited an initial monodisperse droplet size of 1–2 microns, and stability as reflected by a drop in G' of only 11% after 48 hours.

Run 15 illustrates a nonionic, high molecular weight, water soluble, amphipathic, BAB block copolymer emulsifier (PLURONIC-R-25R8). The resulting emulsion is initially polydisperse at 2–8 microns, and the initial G' drops only 7% over 48 hours, indicating good stability.

TABLE 6a

| | Composition of sensors | | | | | |
|---|---|---|---|---|---|---|
| | Stock A | | | | | |
| Run | | Water soluble emulsification enchancement agent | | | | |
| # | Humectant | Type | HLB | Mol. wt. | Stock B | Filler |
| C1 | 5% Starpol 530 | 5% Span 85[1] | 1.8 | 1,100 | DC 7690/7678 | 3% TS-530 |
| C2 | 5% Starpol 530 | 5% G-3300[2] | 11.7 | — | DC 7690/7678 | 3% TS-530 |

TABLE 6a-continued Composition of sensors Stock A

| Run # | Humectant | Water soluble emulsification enchancement agent Type | HLB | Mol. wt. | Stock B | Filler |
|---|---|---|---|---|---|---|
| C3 | 5% Starpol 530 | 5% P4000[3] | — | 4,000 | DC 7690/7678 | 3% TS-530 |
| C4 | none | 5% E-200[4] | — | 200 | DC 7690 | 3% TS-530 |
| 5 | 5% Starpol 530 | 5% Carbowax 3350[5] | — | 3000–3,600 | DC7690 | 3% TS-530 |
| 6 | 5% Starpol 530 | 5% Carbowax 8000[6] | — | 7,000–9,000 | DC 7690 | 3% TS-530 |
| 7 | 5% Starpol 530 | 5% Carbowax 20M[7] | — | 15,000–20,000 | DC 7690 | 3% TS-530 |
| 8 | none | 5% PEO N750[8] | — | 300,000 | DC 7690 | 3% TS-530 |
| 9 | 5% Starpol 530 | 5% P15-200[9] | — | 2,600 | DC 7690/7678 | 3% TS-530 |
| 10 | 5% Starpol 530 | 5% UCON 75-H-90000[10] | — | 15,000 | DC 7690/7678 | 3% TS-530 |
| 11 | 5% Starpol 530 | 5% Tween 20[11] | 16.7 | 1,226 | DC 7690/7678 | 3% TS-530 |
| 12 | 5% Starpol 530 | 5% Hypermer B261[12] | 7–9 | 1,800 | DC 7690/7678 | 3% TS-530 |
| 13 | 5% Starpol 530 | 1% Silwet L77[13] | 5–8 | 600 | DC 7690/7678 | 3% TS-530 |
| 14 | 5% Starpol 530 | 5% Pluronic F108[14] | 27 | 14,600 | DC 7690/7678 | 3% TS-530 |
| 15 | 5% Starpol 530 | 5% Pluronic-R 25R8[15] | 12 | 8,550 | DC 7690/7678 | 3% TS-530 |

[1]"Span 85" is a sorbitan trioleate available from ICI Specialty Chemicals.
[2]"G-3300" is an ionic alkyl aryl sulfonate available from ICI Specialty Chemicals.
[3]"P4000" is a polypropylene oxide available from Dow Chemical Corp.
[4]"E-200" is a polypropylene oxide available from Dow Chemical Corp.
[5]"Carbowax 3350" is a polyethylene oxide available from Union Carbide Corp.
[6]"Carbowax 8000" is a polyethylene oxide available from Union Carbide Corp.
[7]"Carbowax 20M" is a polyethylene oxide available from Union Carbide Corp.
[8]"Polyox N750" is a polyethylene oxide available from Union Carbide Corp.
[9]"P15-200" is a random copolymer of polypropylene oxide and polyethylene oxide available from Dow Chemical Corp.
[10]"UCON 75-H-90000" is a random copolymer of polypropylene oxide and polyethylene oxide available from Union Carbide.
[11]"Tween 20" is a polyoxyethylene (20) sorbitan monolaurate available from ICI Specialty Chemicals.
[12]"Hypermer B261" is an ABA nonionic block copolymer with polyhydroxy fatty acid as the hydrophobe and polyethylene glycol as the hydrophile, available from ICI Specialty Chemicals.
[13]"Silwet L77" is a polyalkylene oxide modified polydimethylsiloxane (block copolymer) available from OSi Specialities.
[14]"Pluronic F108" is a polyethyleneoxide-polypropylene oxide polyethylene oxide block copolymer, available from BASF.
[15]"Pluronic 25R8" is a polypropylene oxide-polyethylene oxide polypropylene oxide block copolymer, available from BASF.

TABLE 6b

Performance of Sensor Emulsions

| Run # | Visual observations on emulsion | Initial droplet size (microns) | Rheology G' (Pa) (initial) | G' (Pa) (48 hrs) | % Change |
|---|---|---|---|---|---|
| C1[1] | Emulsion is well mixed and viscous (not pourable). | Fluorescent held with dark oil droplets (10–20 microns). Emulsion inverted. | failed | failed | failed |
| C2 | Emulsion is well mixed and low viscosity (runny). | 2–4 monodispersed | 83 | 49 | −41.0 |
| C3 | Emulsion was phase separated, low viscosity and pourable with fluorescent sediment. | failed | failed | failed | failed |
| C4 | Unstable emulsion; phase separation. | failed | failed | failed | failed |
| 5 | Emulsion is well mixed, viscous and not pourable. | 2–10 microns, polydispersed | 487 | 248 | −49.1 |

TABLE 6b-continued

Performance of Sensor Emulsions

| Run # | Visual observations on emulsion | Initial droplet size (microns) | Rheology G' (Pa) (initial) | G' (Pa) (48 hrs) | % Change |
|---|---|---|---|---|---|
| | Clear oil layer seen on side of jar (phase separation). | | | | |
| 6 | Emulsion is well mixed, viscous and not pourable. | 2–14 microns, polydispersed | 473 | 210 | –55.6 |
| 7 | Emulsion is well mixed, viscous and not pourable. | 2–4 niicrons, monodispersed | 545 | 301 | –44.8 |
| 8 | Emulsion is well mixed, viscous and not pourable. | 2–4 microns, monodispersed | 405 | 240 | –40.7 |
| 9 | Emulsion is well mixed, viscous and somewhat pourable. | 2–10 microns, polydispersed | 452 | 239 | 47.1 |
| 10 | Emulsion is well mixed, viscous, and not pourable. | 2–8 microns, polydispersed | 458 | 163 | –64.4 |
| 11 | Emulsion is well mixed, viscous and not pourable. | 2–4 microns, monodispersed | 242 | 159 | –34.3 |
| 12 | Emulsion is well mixed, viscous and somewhat pourable. Color is darker due to amber colored Hypermer. | 3–14 microns, polydispersed | 316 | 236 | –25.3 |
| 13 | Emulsion is well mixed, viscous and somewhat pourable. | 2–4 microns, monodispersed | 137 | 129 | –5.8 |
| 14 | Emulsion is well mixed, viscous and not pourable. | 1–2 microns, monodispersed | 557 | 493 | –11.5 |
| 15 | Emulsion is well mixed, viscous and not pourable. | 2–8 microns, polydispersed | 408 | 378 | –7.3 |

[1]This run was mixed using Mixing Method #2; all other runs were mixed using Mixing Method #1.

TABLE 6c

Sensor performance

| | Pre-autoclave | | Post autoclave | |
|---|---|---|---|---|
| Run # | $I_{air}$ | $I_{air}/I_{max}$ | $I_{air}$ | $I_{air}/I_{max}$ |
| C1 | 23,245 | 1.02 | 5828 | 1.03 |
| C2 | — | — | — | — |
| C3 | — | — | — | — |
| C4 | — | — | — | — |
| 5 | — | — | — | — |
| 6 | — | — | — | — |
| 7 | — | — | — | — |
| 8 | — | — | — | — |
| 9 | — | — | — | — |
| 10 | — | — | — | — |
| 11 | 28,732 | .98 | delaminated | — |
| 12 | 28,447 | 1.13 | 24,743 | 1.01 |
| 13 | 24,762 | .94 | 21,428 | .94 |
| 14 | — | — | — | — |
| 15 | — | — | — | — |

Example 7

Effect of the HLB of the Water Soluble Emulsification Enhancement Agent on Sensor Emulsion Stability This example illustrates the wide HLB range of the amphipathic, water soluble emulsification enhancement agent which confers stability to the emulsion. The emulsifiers shown in Table 7a are all nonionic, water soluble, amphipathic ABA block copolymers of the type PEO-PPO-PEO. These emulsifiers cover a range of molecular weights (1,900 to 4,400 Da) and HLB's (1–19), but have been chosen such that the molecular weight of the PEO block is approximately constant at 400–500 Da.

Comparative Run 1 illustrates the use of a classical low HLB, water insoluble emulsifier, namely Pluronic L121. Comparative Run 1 yielded an inverted emulsion of 100 micron oil droplets. The emulsion exhibited low viscosity and was visibly phase separated.

Runs 2 and 3 illustrate the use of higher HLB emulsifiers, namely Pluronic L44 and L35, respectively. Runs 2 and 3, taken in combination with Ex. 1, Run 1, and Example 6, Runs 11–15, illustrate that good emulsion stability is obtained over a wide range of HLB, provided that the HLB is at least 5. This is an unexpected result based upon the conventional rule (Bancroft's rule), which predicts that low HLB emulsifiers (e.g., HLB 1–4, such as L121) are most effective at forming and stabilizing a water in oil emulsion. For a discussion of Bancroft's rule see, Shaw, *Introduction to Colloid & Surface Science*, 3rd Ed., Butterworths, London, 1983, p. 237.

TABLE 7a

Composition of sensors

Stock A

Water soluble emulsification enhancement agent

| Run # | Humectant | Type | HLB | Mol. wt. of PEO block | Stock B | Filler |
|---|---|---|---|---|---|---|
| C1[1] | 5% Starpol 530 | 5% L121 | 1 | 400 | DC 7690 | 3% TS-530 |
| 2 | 5% Starpol 530 | 5% L44 | 16 | 500 | DC 7690 | 3% TS-530 |
| 3 | 5% Starpol 530 | 5% L35 | 19 | 500 | DC 7690 | 3% TS-530 |

[1]Runs 1–3 were mixed using Mixing Method #2.

TABLE 7b

Performance of Sensor Emulsions

| Run # | Visual observations on emulsion | Droplet size (microns) | Rheology G' (Pa) (initial) | G' (Pa) (48 hrs) | % Change |
|---|---|---|---|---|---|
| C1 | Emulsion has a very low viscosity, pourable (runny), grainy and visibly phase separated. | 2–20 polydispersed with dark oil droplets (100 micron). Emulsion inverted. | failed | failed | failed |
| 2 | Emulsion is well mixed, viscous and somewhat pourable. | 2–8 polydispersed | 265 | 210 | –20.8 |
| 3 | Emulsion is well mixed, viscous and somewhat pourable. | 2–10 polydispersed | 306 | 259 | –15.4 |

Example 8

Effect of the Humectant on Sensor Emulsion Stability

This example illustrates the wide range of humectants which can be incorporated into the emulsions in order to obtain additional desirable sensor performance characteristics. These additional characteristics may include improved dry web intensity stability, rapid rehydration of the sensor, and response to dry gas (such as $CO_2$ in the air). In the most preferred case, the humectants are added to the stabilized emulsions as described. As is most evident with the emulsion containing glycerol, trehalose, xanthan gum or Starpol humectants, the absence of the hydrophilic amphipathic emulsifier provides grossly phase separated emulsions immediately after mixing.

In contrast, as shown in Tables 8a and 8b, humectants with weight average molecular weights of 92 Da to 1,000,000 Da can be incorporated into a stable sensor emulsion when a hydrophilic emulsifier is used in conjunction with a water insoluble, colloidal particle (such as silica). This illustrates an additional useful feature of our novel emulsifier system, namely the ability to incorporate a wide range of humectants with varying molecular weights and structures into the same sensor formulation, thereby permitting the sensor performance to be formulated for specific applications. This has also been illustrated in Example 2, and further demonstrates that the choice of humectant is important to achieving autoclavability of the sensor, as measured by the stability of sensor intensities and slopes.

The utility of this approach is further illustrated in Tables 8c and 8d. As shown in these Tables, the choice of humectant is important to achieving manufacturability of precision coated sensors by stabilizing the sensor intensity in a dry coated web. This is important in manufacturing because it extends the shelf life of the web and therefore allows a longer time for the sensor web to be converted into product. Superior intensity stability was demonstrated with sensor emulsions containing xanthan gum (Ex. 8, Run 3) and Starpol (Ex. 8, Run 1) humectants.

In addition to autoclavability and dry web stability, appropriate choice of humectants also gives rise to a new sensor that responds to $CO_2$ from the air (as opposed to tonometered blood or buffer solutions), as shown in Table 8d for Ex. 8 Run 5. The response time is extremely fast, which is a further advantage of this system.

This ability to sense dry gas was not conferred by ethylene oxide, polyethylene oxide, or polysaccharide based humectants (including Starpol, xanthan gum, trehalose, or dextran). It is, however, conferred by glycerol present at 2–99% of the dispersed phase. A dry gas $CO_2$ sensor has utility as a monitor for breath monitoring, monitoring the correct placement of endotracheal tubes, atmospheric industrial monitoring, or for any application for which the sensor is not maintained in equilibrium with water.

TABLE 8a

Composition of sensors

Stock A

| Run # | Humectant | Water soluble emulsification enhancement agent | Stock B | Filler |
|---|---|---|---|---|
| 1[1] | 5% Starpol 560 ($M_w$ ~915,000, $M_n$ ~135,000 Da) | 5% Pluronic F108 | DC7690 | 3% TS-530 |
| 2 | 30% Dextran (500,000 Da) | 5% Pluronic F108 | DC 7690 | 3% TS-530 |
| 3 | 1% xanthan gum (1,000,000 Da) | 4% Pluronic F108 | DC 7690 | 3% TS-530 |
| 4 | 11.4% Trehalose (378 Da) | 5% Pluronic F108 | DC 7690 | 3% TS-530 |
| 5 | 30% glycerol (92 Da) | 5% Pluronic F108 | DC 7690 | 3% TS-530 |
| 6 | 5% PEO (300,000 Da) | none | DC 7690 | 3% TS-530 |

[1] Runs 1–6 were mixed using Mixing Method #1.

TABLE 8b

Performance of Sensor Emulsions

| Run # | Visual observations on emulsion | Droplet size (microns) | Rheology G' (Pa) (initial) | G' (Pa) (48 hrs) | % Change |
|---|---|---|---|---|---|
| 1 | Emulsion is well mixed, viscous and not pourable. | 2–4 monodispersed | 230 | 259 | 12.6 |
| 2 | Emulsion is well mixed, viscous and not pourable. | 2–4 monodispersed | 458 | 439 | −4.51 |
| 3 | Emulsion is well mixed and viscous. | 2–4 monodispersed | 339 | 348 | 2.65 |
| 4 | Emulsion is well mixed and viscous. | 2–6 monodispersed | 371 | 275 | −25.0 |
| 5 | Emulsion is well mixed and viscous. | 2–6 monodispersed | 340 | 331 | 2.65 |
| 6 | Emulsion is well mixed and viscous | 2–4 monodispersed | 405 | 240 | −40.7% |

TABLE 8c

| Run # | Days at room temperature | % Intensity loss |
|---|---|---|
| 1 | 0 | 0 |
|   | 19 | 11 |
|   | 39 | −7 |
| 3 | 0 | 0 |
|   | 19 | −4 |
|   | 39 | −2 |
| 6 | 0 | 0 |
|   | 19 | −20 |
|   | 39 | −27 |

TABLE 8d

| $pCO_2$ | Time (minutes) | Intensity (unreferenced). |
|---|---|---|
| Air | 0 to 3.3 | 295 |
| to 2.8% | 3.4 | 237 |
|  | 3.5 | 198 |
|  | 3.6 | 180 |
|  | 3.7 | 173 |
|  | 3.8 to 6.0 | 172 |
| to 8.4% | 6.2 | 166 |
|  | 6.3 | 166 |
|  | 6.4 | 166 |
|  | 6.5 | 166 |
|  | 6.6 | 123 |
|  | 6.7 to 9.0 | 122 |
| to Air | 9.1 | 167 |
|  | 9.2 | 197 |
|  | 9.3 | 221 |
|  | 9.4 | 240 |
|  | 9.5 | 256 |
|  | 9.6 | 267 |
|  | 9.7 | 277 |
|  | 9.8 | 283 |
|  | 9.9 | 290 |
|  | 10.0 | 293 |
|  | 10.1 to 12.0 | 302 |
| to 2.8% | 12.2 | 215 |
|  | 12.3 | 190 |
|  | 12.4 | 179 |
|  | 12.5 | 174 |
|  | 12.6 to 15.3 | 173 |
| to 8.4% | 15.4 | 150 |
|  | 15.5 | 150 |
|  | 15.6 | 126 |
|  | 15.7 | 123 |
|  | 15.8 to 18.1 | 123 |
| to Air | 18.2 | 149 |
|  | 18.3 | 182 |
|  | 18.4 | 210 |
|  | 18.5 | 232 |
|  | 18.6 | 251 |
|  | 18.7 | 265 |
|  | 18.8 | 274 |
|  | 18.9 | 286 |
|  | 19.0 | 290 |
|  | 19.5 to 21.0 | 304 |

Example 9

Preparation of Sensors

A sensor emulsion was prepared by dispersing a first phase (Stock A) into a second phase comprising a hydrophobic silicone. To form the emulsion, 50 parts Stock A was mixed with 100 parts Dow Corning 7690 vinyl silicone polymer and 3 parts of a water insoluble emulsification enhancement agent (Cabosil TS-720 silica).

Stock A was prepared by mixing the following components: 50 parts glycerol; 40 parts polyethylene glycol-600; 10 parts of a 1M $Na_2CO_3$ solution in water (to achieve a 100 mM $Na_2CO_3$ level); 0.21 parts HPTS (to achieve a 4 mM level); and 0.24 parts glycerophosphoric acid disodium salt (to achieve an 8 mM level). The emulsion was formed by homogenizing for 30 seconds with a Tissue-Tearor mixer operating at maximum RPM.

A 0.5 gram aliquot of the resulting emulsion was removed and 20 microliters of a UV-activated hydrosilation catalyst was added. One drop (~0.03 gm) of Dow Corning 7678 silyl hydride crosslinker was then added and stirred in. The mixture was briefly degassed under vacuum, then cast into the wells of a standard sensing cartridge. The assembly was held under a UV sunlamp for three minutes to facilitate curing of the emulsion.

The sensing cartridge was then placed on a monitoring fixture and intensity under conditions of exposure to ambient room air was then measured as 1070 counts. The sensor was then placed in a dry 60° C. oven overnight and then held in ambient air for two days, after which the ambient air intensity was measured as 1066 counts. The sensor was again held in ambient air for 7 and for 30 additional days. The intensity was 1021 and 1008, respectively. The sensor thus displayed a stable and effective signal when stored under exposure to ambient air.

Various modifications and alterations of this invention will be apparent to those skilled in the art without departing from the scope and spirit of this invention, and it should be understood that this invention is not limited to the illustrative embodiments set forth herein.

What is claimed is:

1. A gas sensing composition, comprising:

a dispersed first phase comprising droplets which are substantially smaller in at least one dimension than the thickness of the sensing composition, wherein the first phase contains at least one substantially water soluble emulsification enhancement agent; at least one water soluble indicator component effective to provide a signal in response to the concentration of a gas in a medium to which the sensing composition is exposed, and a humectant; and a hydrophobic second phase which is permeable to the analyte and impermeable to ionized hydrogen, wherein the second phase contains at least one substantially water insoluble emulsification enhancement agent.

2. A gas sensing composition according to claim 1, wherein the water soluble emulsification enhancement agent comprises a nonionic, amphipathic copolymer having a weight average molecular weight between 500 and 20,000.

3. A gas sensing composition according to claim 1, wherein the water soluble emulsification enhancement agent comprises a nonionic, amphipathic copolymer and is present in a concentration of between 0.01 and 5 weight % in the sensing composition.

4. A gas sensing composition according to claim 1, wherein the second phase comprises a carbon dioxide permeable polymeric material.

5. A gas sensing composition according to claim 1, wherein the second phase is a silicone material.

6. A gas sensing composition according to claim 1, wherein the humectant is a water soluble molecule with weight average molecular weight below 4 million.

7. A gas sensing composition according to claim 1, wherein the humectant is selected from the group consisting of: hydroxypropyl starch, hydroxyethyl starch, dextran, polyvinylalcohol, glycerol, polyvinylpyrrolidone, xanthan gum, gum arabic, methyl cellulose, tragacanth, acacia, agar, pectin, sodium alginate, alginate derivatives, proteins, gelatins, guar gum, polyethylene glycol, polyethylene oxide, and hydrogels.

8. A gas sensing composition according to claim 1, wherein the humectant is thermally stable at temperatures up to 121° C. for 1 hour.

9. A gas sensing composition according to claim 1, wherein the humectant provides a sensor having a shorter equilibration time when the sensor is moved from a dry environment to a humid or aqueous environment compared to a sensor that does not contain a humectant.

10. A gas sensing composition according to claim 1, wherein the humectant is present in an amount between about 0.5 and 99% by weight of the dispersed phase.

11. A gas sensing composition according to claim 1, wherein the humectant is present in an amount between 1 and 70% by weight of the dispersed phase.

12. A gas sensing composition according to claim 1, wherein the humectant is present in an amount between 5 and 30% by weight of the dispersed phase.

13. A gas sensing composition according to claim 1, wherein the indicator component is a pH sensitive dye.

14. A gas sensing composition of claim 1, wherein the indicator component is selected from the group consisting of: hydroxypyrene trisulfonic acid, and salts of hydroxypyrene trisulfonic acid.

15. A gas sensing composition according to claim 1, wherein the volume of the aqueous phase occupies 10 to 60% of the sensing composition.

16. A gas sensing composition according to claim 1, wherein the hydrophobic particles are present in a concentration of between 0.1 and 20 weight % in the sensing composition.

17. A gas sensing composition according to claim 1, wherein the initial elastic modulus of the uncured emulsion is greater than 100 Pa and the equilibrium elastic modulus at 48 hours is greater than 100 Pa.

18. A gas sensing composition according to claim 1, wherein the dispersed first phase further includes a buffer and an osmoregulatory agent.

19. A gas sensing composition according to claim 18, wherein the buffer is selected from the group consisting of bicarbonate or phosphate ion based buffer solution.

20. A gas sensing composition according to claim 18, wherein the dispersed first phase has a pH from about 5 to 14.

21. A gas sensing composition according to claim 1, wherein the water soluble emulsification enhancement agent comprises a nonionic, amphipathic copolymer containing both hydrophilic and hydrophobic moieties.

22. A gas sensing composition according to claim 21, wherein the hydrophilic moiety is polyethylene oxide and the hydrophobic moiety is polypropylene oxide.

23. A gas sensing composition according to claim 21, wherein the water soluble emulsification enhancement agent is an ABA block copolymer, wherein the A block is a polyethylene oxide molecule and the B block is polypropylene oxide molecule.

24. A gas sensing composition according to claim 21, wherein the water soluble emulsification enhancement agent is a BAB block copolymer, wherein the A block is a polyethylene oxide molecule and the B block is polypropylene oxide molecule.

25. A gas sensing composition according to claim 21, wherein the water soluble emulsification enhancement agent has an HLB of at least 5.

26. A gas sensing composition according to claim 21, wherein the water soluble emulsification enhancement agent has an HLB of at least 10.

27. A gas sensing composition according to claim 21, wherein the water soluble emulsification enhancement agent has a weight average molecular weight between 100 and 50,000.

28. A gas sensing composition according to claim 21, wherein the droplets have an average size less than 5 microns.

29. A gas sensing composition according to claim 21, wherein the initial elastic modulus of the uncured emulsion is greater than 200 Pa and the equilibrium elastic modulus at 48 hours is greater than 200 Pa.

30. A gas sensing composition according to claim 21, wherein the water insoluble emulsification enhancement agent comprises a plurality of dispersed hydrophobic particles.

31. A gas sensing composition according to claim 30, wherein the hydrophobic particles have a mean volume particle size less than 5 microns.

32. A gas sensing composition according to claim 30, wherein the hydrophobic particles comprise surface treated colloidal silica.

33. A gas sensing composition according to claim 30, wherein the hydrophobic particles are chemically bonded to the hydrophobic second phase.

34. A gas sensing composition according to claim 30, wherein the second phase comprises polydimethylsiloxane.

35. A gas sensing composition according to claim 30, wherein the initial elastic modulus of the uncured emulsion is greater than 300 Pa and the equilibrium elastic modulus at 48 hours is greater than 300 Pa.

36. A sensor for measuring the concentration of an analyte in a medium comprising:

a sensing element comprising a sensing composition according to claim 1;

an excitation assembly positioned and adapted to provide an excitation signal to the sensing element;

a detector assembly positioned and adapted to detect an emitted signal from the sensing element, the sensing element being capable of providing the emitted signal in response to being exposed to the excitation signal; and a processor assembly positioned and adapted to analyze the emitted signal in determining the concentration of the analyte in the medium.

37. A sensor for measuring the concentration of an analyte in a medium comprising:

a sensing element comprising a sensing composition according to claim 30;

an excitation assembly positioned and adapted to provide an excitation signal to the sensing element;

a detector assembly positioned and adapted to detect an emitted signal from the sensing element, the sensing element being capable of providing the emitted signal in response to being exposed to the excitation signal; and a processor assembly positioned and adapted to analyze the emitted signal in determining the concentration of the analyte in the medium.

38. A dry gas sensing composition, comprising:

a dispersed first phase comprising droplets which are substantially smaller in at least one dimension than the thickness of the sensing composition, wherein the first phase contains a humectant and at least one soluble indicator component effective to provide a signal in response to the concentration of an analyte in a medium to which the sensing composition is exposed; and a hydrophobic second phase which is permeable to the analyte and impermeable to ionized hydrogen, wherein the sensing composition provides an effective signal in response to the gas when the medium is dry.

39. A dry gas sensing composition according to claim 38, wherein the first phase comprises at least 20 percent by weight humectant.

40. A dry gas sensing composition according to claim 38, wherein the first phase comprises at least 70 percent by weight humectant.

41. A dry gas sensing composition according to claim 38, wherein the first phase further contains at least one substantially water soluble emulsification enhancement agent comprising a nonionic, amphipathic copolymer containing both hydrophilic and hydrophobic moieties, and the second phase further contains at least one substantially water insoluble emulsification enhancement agent comprising a plurality of dispersed hydrophobic particles.

42. A sensor for measuring the concentration of an analyte in a medium comprising:

a sensing element comprising a sensing composition according to claim 38;

an excitation assembly positioned and adapted to provide an excitation signal to the sensing element;

a detector assembly positioned and adapted to detect an emitted signal from the sensing element, the sensing element being capable of providing the emitted signal in response to being exposed to the excitation signal; and a processor assembly positioned and adapted to analyze the emitted signal in determining the concentration of the analyte in the medium.

43. A dry gas sensing composition, comprising:

a dispersed first phase comprising droplets which are substantially smaller in at least one dimension than the thickness of the sensing composition, wherein the first phase contains glycerol and at least one soluble indicator component effective to provide a signal in response to the concentration of an analyte in a medium to which the sensing composition is exposed; and a hydrophobic second phase which is permeable to the analyte and impermeable to ionized hydrogen, wherein the sensing composition provides an effective signal in response to the gas when the medium is dry.

44. A dry gas sensing composition according to claim 43, wherein the first phase comprises at least 30 percent by weight glycerol.

45. A dry gas sensing composition according to claim 43, wherein the first phase comprises at least 50 percent by weight glycerol.

46. A dry gas sensing composition according to claim 43, wherein the first phase further contains at least one substantially water soluble emulsification enhancement agent comprising a nonionic, amphipathic copolymer containing both hydrophilic and hydrophobic moieties, and the second phase further contains at least one substantially water insoluble emulsification enhancement agent comprising a plurality of dispersed hydrophobic particles.

47. A sensor for measuring the concentration of an analyte in a medium comprising:

a sensing element comprising a sensing composition according to claim 43;

an excitation assembly positioned and adapted to provide an excitation signal to the sensing element;

a detector assembly positioned and adapted to detect an emitted signal from the sensing element, the senshg element being capable of providing the emitted signal in response to being exposed to the excitation signal; and a processor assembly positioned and adapted to analyze the emitted signal in determining the concentration of the analyte in the medium.

* * * * *